US009717659B2

(12) United States Patent
Fernandez Botello et al.

(10) Patent No.: US 9,717,659 B2
(45) Date of Patent: Aug. 1, 2017

(54) LIPOSOMES FOR THE TREATMENT OF TEXTILE MATERIALS

(75) Inventors: Alfonso Fernandez Botello, Malaga (ES); Joseph-Lluis Viladot Petit, Barcelona (ES); Raquel Delgado Gonzalez, Gava Barcelona (ES)

(73) Assignee: Lipotec, S.A., Gava, Barcelona (ES)

( * ) Notice: Subject to any disclaimer, the term of this patent is extended or adjusted under 35 U.S.C. 154(b) by 658 days.

(21) Appl. No.: 13/588,855

(22) Filed: Aug. 17, 2012

(65) Prior Publication Data
US 2013/0183358 A1  Jul. 18, 2013

Related U.S. Application Data

(63) Continuation-in-part of application No. PCT/EP2011/000778, filed on Feb. 18, 2011.

(30) Foreign Application Priority Data

Feb. 18, 2010  (ES) .................................. 201030229

(51) Int. Cl.
| | | |
|---|---|---|
| *A61K 9/127* | (2006.01) | |
| *A61K 8/14* | (2006.01) | |
| *A61K 8/81* | (2006.01) | |
| *A61Q 19/00* | (2006.01) | |
| *C11D 3/36* | (2006.01) | |
| *C11D 17/00* | (2006.01) | |
| *D06M 13/292* | (2006.01) | |
| *A61Q 7/02* | (2006.01) | |
| *A61Q 17/04* | (2006.01) | |
| *C11D 3/22* | (2006.01) | |

(Continued)

(52) U.S. Cl.
CPC .............. *A61K 8/14* (2013.01); *A61K 8/8182* (2013.01); *A61K 9/1271* (2013.01); *A61Q 7/02* (2013.01); *A61Q 17/04* (2013.01); *A61Q 19/00* (2013.01); *C11D 3/227* (2013.01); *C11D 3/362* (2013.01); *C11D 3/364* (2013.01); *C11D 3/3723* (2013.01); *C11D 3/3742* (2013.01); *C11D 3/3769* (2013.01); *C11D 3/38* (2013.01); *C11D 17/0039* (2013.01); *D06M 13/292* (2013.01); *A61K 2800/10* (2013.01)

(58) Field of Classification Search
CPC ..................................................... A61K 9/127
USPC ........................................................ 424/450
See application file for complete search history.

(56) References Cited

U.S. PATENT DOCUMENTS

| | | |
|---|---|---|
| 4,774,231 A | 9/1988 | Petitou et al. |
| 4,975,441 A | 12/1990 | Gibson |
| | (Continued) | |

FOREIGN PATENT DOCUMENTS

| | | |
|---|---|---|
| DE | 19727508 | 1/1998 |
| DE | 102004017996 | 11/2005 |
| | (Continued) | |

OTHER PUBLICATIONS

Schabb. Happi, May 1986, p. 84-86, "Impregnating Fabrics With Microcapsules.".

(Continued)

*Primary Examiner* — Gollamudi Kishore
(74) *Attorney, Agent, or Firm* — Fay Sharpe LLP

(57) ABSTRACT

Liposomes with cosmetic and/or dermopharmaceutical ingredients for the care of the skin, scalp and/or hair and their use in washing agents and/or sprays for the treatment of textile materials.

8 Claims, 5 Drawing Sheets

(51) Int. Cl.
*C11D 3/37* (2006.01)
*C11D 3/38* (2006.01)

(56) References Cited

U.S. PATENT DOCUMENTS

| | | |
|---|---|---|
| 5,015,470 A | 5/1991 | Gibson |
| 5,081,151 A | 1/1992 | Davis et al. |
| 2005/0058700 A1 | 3/2005 | Wachter et al. |
| 2005/0266065 A1* | 12/2005 | Perrier et al. .......... 424/450 |
| 2007/0053918 A1 | 3/2007 | Panzner et al. |
| 2008/0234507 A1* | 9/2008 | Viladot Petit ............ A61K 8/11 554/1 |
| 2008/0317795 A1 | 12/2008 | Traynor et al. |
| 2009/0011003 A1* | 1/2009 | Yamauchi ............ A61K 9/127 424/450 |
| 2009/0285882 A1* | 11/2009 | Weiss .................... A23L 3/3463 424/450 |

FOREIGN PATENT DOCUMENTS

| | | |
|---|---|---|
| EP | 0211610 | 2/1981 |
| EP | 0064012 | 11/1982 |
| EP | 0277428 | 8/1988 |
| EP | 0334586 | 9/1989 |
| EP | 0375388 | 6/1990 |
| EP | 1510619 | 3/2005 |
| EP | 1972324 | 9/2008 |
| ES | 2206726 T3 | 5/2004 |
| WO | 2008/089707 * | 7/2008 |

OTHER PUBLICATIONS

Gottschalck et al. International Cosmetic Ingredient Dictionary and Handbook, 12th edition 2008, vol. 3, 14 Pages, "Biological Polymers and their Derivatives (Including salts, excluding gums, hydrophilic colloids and derivatives).".

Nelson. "Application of Microencapsulation in Textiles", International Journal of Pharmaceutics 2002, vol. 242, p. 55-62.

Hipler et al. Biofunctional Textiles and the Skin 2006, vol. 33, 10 Pages, "Current Problems in Dermatology.".

Malcolm et al. "Controlled Release of Model Antibacterial Drug From a Novel Self-Lubricating Silicone Biomaterial", Journal of Controlled Release 2004, vol. 97, p. 313-320.

Pignatello, "Drug-Biomembrane Interaction Studies: The Application of Calorimetric Techniques," p. 59 (2013).

* cited by examiner

LIPOSOMES FOR THE TREATMENT OF TEXTILE MATERIALS

CROSS-REFERENCE TO RELATED APPLICATIONS

This application is continuation-in-part of U.S. national phase of PCT Appln. No. PCT/EP2011/000778 filed Feb. 18, 2011 which claims priority to Spanish application 201030229 filed Feb. 18, 2010, the disclosures of which are incorporated in their entirety by reference herein.

FIELD OF THE INVENTION

This invention relates to microfluidized liposomes which contain cosmetic and/or dermopharmaceutical agents wherein these liposomes are coated with a cationic polymer which conserves the positive charge necessary for an effective adsorption of the liposomes in natural or synthetic fibers. The release of the liposomes and therefore the cosmetic and/or dermopharmaceutical agents which contain these liposomes is carried out through the standard methods of pressure, skin pH, friction, osmosis or heat.

PRIOR ART

This invention refers to liposomes with cosmetic and/or dermopharmaceutical ingredients for the care of the skin, scalp and/or hair. The cationic polymers on the surface of the liposomes allow their effective linking to the fibers of the textile material.

The preparation of textile materials with chemical products linked to them has been extensively studied to provide textile materials with cosmetic and/or dermopharmaceutical purposes, i.e. textile materials which release cosmetic and/or dermopharmaceutical agents in contact with the skin. However, there is the need in the prior art for the aforementioned cosmetic and/or dermopharmaceutical active ingredients to have a greater permanence on the textile material than at present, since the delivery systems which contain these active ingredients are separated from the textile material after a few washes.

Surprisingly we have found that certain cationic polymers bound to liposomes link to the surface of the textile material on several points forming a net or mesh-like structure. The liposomes coated with cationic polymers, which we propose in this invention are a solution open to any cosmetic and/or dermopharmaceutical active ingredient and have sufficient stability to remain attached to the textile material, both natural and synthetic, after several washes.

DESCRIPTION

This invention relates to liposomes which contain cosmetic and/or dermopharmaceutical active ingredients and/or adjuvants, and which are linked to cationic polymers, wherein these polymers form a network over the surface of the textile material when they are brought into contact with textile material. This network on the surface of the textile material enables a more effective linking of the liposomes to the textile material than in the case of the liposomes known in the prior art.

Liposomes are a commonly used solution which prolongs the period of availability of an active agent. The material on the wall of the liposome presents a resistance and thermal stability that are such that the liposome is not destroyed under storage conditions, but the mechanical release of the encapsulated substances is enabled under light pressure action, or thermal release at a temperature of 35 to 220° C. Another possibility consists of the liposome wall becoming semi-permeable in its properties through its modification such as from pressure, friction or heat.

In this invention the term "liposome" relates to an approximately spherical aggregate formed by at least a double layer or bilayer of at least one phospholipid wherein the layers are very close and the apolar regions of each layer face the apolar regions of the other lipid layer, and thus the polar regions of the phospholipids form the internal and external face of the double layer or bilayer. The liposomes of this invention can have just one bilayer and are structured like unilaminar liposomes, or they can have from 2 to 6 bilayers, concentric or non-concentric, of lipids, preferably from 2 to 4 concentric bilayers, and will then be organized as multilaminar liposomes like onions, or can have from 2 to 6 bilayers and be organized like unilaminar liposomes which are comprised of 1 to 5 smaller unilaminar liposomes. The liposomes in this invention present a nucleus which can contain a series of hydrophilic cosmetic and/or dermopharmaceutical active ingredients, and at least a lipid bilayer which can contain hydrophobic cosmetic and/or dermopharmaceutical active ingredients.

In a particular embodiment, the phospholipid of the liposomes of this invention is a natural or synthetic phosphoglyceride and is preferably selected from the group formed by phosphatidylserine, phosphatidylinositol, phosphatidylethanolamine, phosphatidylcholine, phosphatidic acid, phosphatidylglycerol, diphosphatidylglycerol, phosphorylcholine, cardiolipin, their fatty acid esters, hydrogenation products and mixtures thereof, such as and not restricted to natural lecithins such as that from an egg, soy or sunflower. Among the fatty acids are found, for example and not restricted to, stearic, palmitic, oleic, myristic, lauric acid and any saturated or unsaturated fatty acids known in the prior art. Preferably, the phospholipids used are phosphatidylcholine, phosphatidylethanolamine and phosphatidylinositol.

In a particular embodiment, the liposomes are mixed liposomes formed by one or more phospholipids and one or more homogeneously distributed surfactants in each of the double layers or bilayers and with the aforementioned described structures for the liposomes. In particular, the surfactant of these mixed liposomes is selected from the group formed by non-ionic surfactants, amphoteric surfactants, anionic surfactants, cationic surfactants and mixtures thereof. Preferably, the surfactants are non-ionic surfactants and/or amphoteric surfactants, more preferably they are selected from the group formed by alkylglycosides with an alkyl group which has from 6 to 24 carbon atoms, alkylmaltosides with an alkyl group which has from 6 to 24 carbon atoms, ethoxylated alkylphenols with an alkyl group which has from 6 to 24 carbon atoms and from 5 to 30 units of ethylene oxide, alkyl phenyl polyoxyethylene ethers with an alkyl group which has from 6 to 24 carbon atoms, saturated or unsaturated fatty alcohols with an alkyl group which has 8 to 24 carbon atoms, poloxamers, polysorbates, sorbitan esters, polyethylene glycol fatty acid esters, ricin oils, fatty alcohol and polyoxyethylene ethers, fatty acid alkanolamides, amine oxides, alkyl betaines with an alkyl group which has from 6 to 24 carbon atoms, acyl amido betaines, alkyl sulfobetaines with an alkyl group which has from 6 to 24 carbon atoms, glycine derivatives, digitonin and mixtures thereof. More preferably they are selected from the group formed by octyl glucoside, decyl glucoside, lauryl glucoside, octyl fructoside, dodecyl maltoside, decyl maltoside, nonoxynol-9, polyethylene glycol p-(1,1,3,3-tetramethylbutyl)phenyl ether, palmityl alcohol, oleyl alcohol, poloxamer 188, poloxamer 407, polysorbate 20, polysorbate 60, polysorbate 80, polyethylene glycol stearate 40, polyethylene glycol stearate 50, polyethylene glycol stearate 100, polyoxyethylene stearyl ether, polyoxyethylene lauryl ether, cocamide monoethanolamine, cocamide diethanolamine, cocamide triethanolamine, lauramide diethanolamine, lauramide monoethanolamine, cocamidopropylamine oxide, decyl betaine, dodecyl betaine, tetradecyl betaine, cocoyl betaine, cocamidopropyl betaine, cocamidopropyl hydroxysultaine, cocoyl amidoethyl N-2-hydroxyethylglycinate and N-cocoyl amidoethyl 2-hydroxyethylcarboxyglycinate and mixtures thereof.

In another particular embodiment, the cationic polymers bound to the liposomes are natural or synthetic polymers, for example, cationic derivatives of cellulose, such as quaternized hydroxyethylcellulose, which can be acquired under the name Polymer JR 400™ by Amerchol, cationic starches, copolymers of diallylammonium and acrylamide salts, quaternized vinylpyrrolidone/vinylimidazole polymers such as Luviquat™ (BASF), condensation products of polyglycols and amines, polyquaternium polymers and copolymers, polymers named Merquats of polyquaternium-6, polyquaternium-7; polyquaternium-16, polyquaternium-10, polyquaternium-4 copolymers, dicocoylethylhydroxyethylammonium, graft copolymers with a cellulose backbone and quaternary ammonium groups, quaternized collagen polypeptides such as lauryldimethylammonium hydroxypropyl hydrolyzed collagen (Lamequat™ by Grünau), quaternized wheat polypeptides, polyethylenimine, cationic silicone polymers such as amodimethicone or silicone quaternium-22, adipic acid and dimethylamino hydroxypropyldiethylenetriamine copolymers (Cartaretine™ by Sandoz), copolymer of dimethyldiallylammonium chloride and acrylic acid (Merquat™ 550 by Chemviron), cationic chitin derivatives such as chitosan and its derivatives, condensation products of cationic dihalogen alkylene such as dibromobutane with bisdialkylamines such as bis-dimethylamino-1,3-propane, derivatives of cationic guar gum such as guarhydroxypropyltriammonium, Jaguar™ CBS, Jaguar™ C-17, Jaguar™ C-16 by Celanese, quaternary ammonium salt polymers such as Mirapol™ A-15, Mirapol™ AD-1, Mirapol™ AZ-1 by Miranol, quaternized polysaccharide polymers from natural derivatives such as agar, cationic proteins selected from among gelatin, gum arabic; cationic polymers from the group formed by polyamides, polycyanoacrylates, polylactides, polyglycolides, polyaniline, polypyrrole, polyvinylpyrrolidone, amino silicone polymers and copolymers, polystyrene, polyvinylic alcohol, polystyrene and maleic acid anhydride copolymers, methyl vinyl ether, epoxy resins, and styrene and methyl methacrylate copolymers; dimethylamino methacrylate, polyacrylates and cationic polymethacrylates such as Eudragit™ RL 30 D by R $\vec{o}$hm; derivatives of polyamine optionally substituted by the derived members of polyethylene glycol; polyamine acids under pH conditions wherein they are cationic; polyethyleneimine; quaternized derivatives of polyvinylpyrrolidone (PVP) and hydrophilic urethane polymers, as well as any mixture of the aforementioned cationic groups.

The liposomes of this invention which contain cosmetic and/or dermopharmaceutical active ingredients and/or adjuvants can be applied to the natural or synthetic fibers of textile materials before or after manufacture. In this invention textile materials are understood to be fabrics, non-woven fabrics, garments and medical devices. Examples of fabrics, non-woven fabrics, garments, medical devices and means for immobilization of liposomes can be found in the literature and are known in the prior art ("Impregnating Fabrics With Microcapsules", HAPPI May 1986; Int. J. Pharm. 2002, 242, 55-62; "Biofunctional Textiles and the Skin" Curr. Probl. Dermatol. 2006 v.3; J. Cont. Release 2004, 97, 313-320). Preferred means for immobilizing liposomes in textile materials are carried out through application using washing agents or the use of sprays without needing to soak the textile materials. Surprisingly this invention provides a considerable improvement on the binding of liposomes to the natural or synthetic fibers of the surface of the textile material during a prolonged period due to the network structure that the cationic polymers form on the textile material in relation to the liposomes bound to cationic monomers known in the prior art. The natural and/or synthetic fibers can be wool, cotton, silk, nylon fibers, cellulose or polyester, among others. Among the textile materials the preferred woven fabrics, non-woven fabrics, garments and medical devices are bandages, gauzes, t-shirts, socks, tights, underwear, girdles, gloves, diapers, sanitary napkins, dressings, bedspreads, wipes, hydrogels, adhesive patches, non-adhesive patches, micro-electric patches and/or face masks.

By means of the use of textile materials with adsorbed liposomes, the cosmetic and/or dermopharmaceutical active ingredients and/or adjuvants contained in the liposomes can be transferred to the skin, scalp and/or hair, after the skin, scalp and/or hair have been brought into contact with the liposome, through mechanical pressure, friction, osmosis or heat. In practice, the liposomes of the invention either due to biodegradation of the linking system to the textile material or due to friction between the textile material and the body, or due to body moisture or due to the body temperature, release the cosmetic and/or dermopharmaceutical active ingredients and/or adjuvants. The resulting phospholipids and the cosmetic and/or dermopharmaceutical active ingredients and/or adjuvants form a fine film on the surface of the textile materials which facilitates contact with the skin, scalp and/or hair and subsequently the transfer of the active ingredients and/or adjuvants through mechanical processes such as friction.

In addition, the cationic polymers bound to the liposomes modify their structure making them more flexible, which also allows the liposomes to cross or penetrate the skin, scalp and/or hair with greater ease, thus increasing the penetration of the cosmetic and/or dermopharmaceutical active ingredients and/or adjuvants.

Furthermore, if the liposomes of this invention undergo micro-fluidification, which allows homogenization of the liposomes through high pressure, smaller sized liposomes are obtained which affords them greater stability and consistency in comparison with the liposomes which have not undergone micro-fluidification.

In particular, the cationic polymer has positive charges which electrostatically interact with the phosphate group of the phospholipids which form the lipid membrane of the liposomes. Therefore, the same cationic polymer can interact with several liposomes at once forming a framework or network of liposomes whose overall charge is positive and which are linked to the surface of the textile materials at several points.

Cryomicroscopy and laser light scattering LLS assays show that this framework or network includes several liposomes within the same cationic polymeric network where the size of the cationic polymer is in the region of 600-1700 nm, in comparison with the size of the liposomes which are smaller or equal to 300 nm, in particular, smaller than 200 nm.

According to another aspect of this invention, the inside of the liposomes contains cosmetic and/or dermopharmaceutical active ingredients and/or adjuvants. In particular, the cosmetic and/or dermopharmaceutical active ingredients and/or adjuvants for the treatment and/or care of the skin, scalp and/or hair are selected, for example and not restricted to, the group formed by surfactants, humectants or substances which retain moisture, emollients, moisturizers, agents stimulating healing, coadjuvant healing agents, agents stimulating re-epithelialization, coadjuvant re-epithelialization agents, agents stimulating the synthesis of dermal or epidermal macromolecules, firming and/or redensifying and/or restructuring agents, cytokine growth factors, agents acting on capillary circulation and/or microcirculation, anti-glycation agents, free radical scavengers and/or anti-atmospheric pollution agents, reactive carbonyl species scavengers, 5α-reductase inhibiting agents, lysyl- and/or prolyl hydroxylase inhibiting agents, defensin synthesis-stimulating agents, bactericidal agents and/or bacteriostatic agents and/or antimicrobial agents and/or germicidal agents and/or fungicidal agents and/or fungistatic agents and/or germ-inhibiting agents, anti-viral agents, antiparasitic agents, anti-histaminic agents, NO-synthase inhibiting agents, desquamation agents or keratolytic agents and/or exfoliating agents, comedolytic agents, anti-psoriasis agents, anti-inflammatory agents and/or analgesics, anesthetic agents, anti-wrinkle and/or anti-aging agents, cosmetic deodorants and/or absorbent and/or body odor masking deodorants, antiperspirant agents, perfuming substances and/or perfumed oils and/or isolated aromatic compounds, anti-oxidizing agents, agents inhibiting vascular permeability, hydrolytic epidermal enzymes, whitening or skin depigmenting agents, agents inhibiting sweat-degrading enzymes, agents capable of filtering UV rays, agents which stimulate or regulate the differentiation of keratinocytes, anti-itching agents, agents which stimulate or inhibit the synthesis of melanin, propigmenting agents, self-tanning agents, agents stimulating the proliferation of melanocytes, liquid propellants, vitamins, amino acids, proteins, biopolymers, gelling polymers, skin relaxant agents, agents capable of reducing or treating bags under eyes, agents for the treatment and/or care of sensitive skin, astringent agents, agents regulating sebum production, anti-stretch mark agents, lipolytic agents or agents stimulating lipolysis, venotonic agents, anti-cellulite agents, calming agents, agents acting on cell metabolism, agents to improve dermal-epidermal junction, agents inducing hair growth or hair-loss retardant agents, body hair growth inhibiting or retardant agents, heat shock protein synthesis stimulating agents, muscle relaxants, muscle contraction inhibiting agents, agents inhibiting the aggregation of acetylcholine receptors, anticholinergic agents, elastase inhibiting agents, matrix metalloproteinase inhibiting agents, chelating agents, vegetable extracts, essential oils, marine extracts, mineral salts, cell extracts, emulsifying agents, agents stimulating the synthesis of lipids and components of the stratum corneum (ceramides, fatty acids, etc.), agents obtained from a bio-fermentation process and/or mixtures thereof. The nature of these cosmetic and/or dermopharmaceutical agents and/or adjuvants can be synthetic or natural, such as vegetable extracts, or come from a biotechnological process or from a combination of a synthetic process and a biotechnological process. Additional examples can be found in the CTFA International Cosmetic Ingredient Dictionary & Handbook, 12th Edition (2008). In the context of this invention, a biotechnological process is understood to be any process which produces the active ingredient, or part of it, in an organism, or in a part of it.

In a particular embodiment the surfactant which may be contained in the liposomes of this invention is any of the aforementioned surfactants which form the mixed liposomes.

In a particular embodiment, the humectant or substance that retains moisture, moisturizer or emollient which can be contained in the liposomes of this invention is selected, for example and not restricted to, from the group formed by polyols and polyethers such as glycerin, ethylhexylglycerin, caprylyl glycol, pentylene glycol, butylene glycol, propylene glycol and their derivatives, triethylene glycol, polyethylene glycol, Glycereth-26, Sorbeth-30; panthenol; pyroglutamic acid and their salts and derivatives; amino acids, such as serine, proline, alanine, glutamate or arginine; ectoine and its derivatives; N-(2-hydroxyethyl)acetamide; N-lauroyl-pyrrolidonecarboxylic acid; N-lauroyl-L-lysine; N-alpha-benzoyl-L-arginine; urea; creatine; α- and β-hydroxy acids such as lactic acid, glycolic acid, malic acid, citric acid or salicylic acid, and their salts; polyglyceryl acrylate; sugars and polysaccharides, such as glucose, saccharide isomerate, sorbitol, pentaerythritol, inositol, xylitol, trehalose and derivatives thereof, sodium glucuronate, carrageenans (*Chondrus crispus*) or chitosan; glycosaminoglycans such as hyaluronic acid and derivatives thereof; aloe vera in any of its forms; honey; soluble collagen; lecithin and phosphatidylcholine; ceramides; cholesterol and its esters; tocopherol and its esters, such as tocopheryl acetate or tocopheryl linoleate; long-chain alcohols such as cetearyl alcohol, stearyl alcohol, cetyl alcohol, oleyl alcohol, isocetyl alcohol or octadecan-2-ol; long-chain alcohol esters such as lauryl lactate, myristyl lactate or C12-C15 alkyl benzoates; fatty acids such as stearic acid, isostearic acid or palmytic acid; polyunsaturated fatty acids (PUFAs); sorbitans such as sorbitan stearate; glycerides such as glyceryl monoricinoleate, glyceryl monostearate, glyceryl stearate citrate or caprylic or capric acid triglyceride; saccarose esters such as saccarose palmitate or saccarose oleate; butylene glycol esters, such as dicaprylate and dicaprate; fatty acids such as isopropyl isostearate, isobutyl palmitate, isocetyl stearate, isopropyl laurate, hexyl laurate, decyl oleate, cetyl palmitate, di-n-butyl sebacate, isopropyl myristate, isopropyl palmitate, isopropyl stearate, butyl stearate, butyl myristate, isopropyl linoleate, 2-ethylhexyl palmitate, 2-ethylhexyl cocoate, decyl oleate, myristyl myristate; squalene; mink oil; lanolin and its derivatives; acetylated lanolin alcohols; silicone derivatives such as cyclomethicone, dimethicone or dimethylpolysiloxane; Antarcticine® [INCI: *Pseudoalteromonas* Ferment Extract] or acetyl-glutamyl-methionyl-alanyl-iso-leucine, acetyl-arginyl-phenylglycyl-phenylglycine or acetyl-arginyl-6-aminohexanoyl-alanine marketed by Lipotec, petrolatum; mineral oil; mineral and synthetic waxes; beeswax (*cera alba*); paraffin; or waxes and oils with vegetable origins such as candelilla wax (*Euphorbia cerifera*), carnauba wax (*Copernicia cerifera*), shea butter (*Butirospermum parkii*), cocoa butter (*Theobroma cacao*), castor oil (*Ricinus communis*), sunflower oil (*Helianthus annuus*), olive oil (*Olea europaea*), coconut oil (*Cocos nucifera*), palm oil (*Elaeis guineensis*), wheat germ oil (*Triticum vulgare*), sweet almond oil (*Prunus amygdalus dulces*), musk rose oil (*Rosa moschata*), soya bean oil (*Glycine soja*), grape seed oil (*Vitis vinifera*), calendula oil (*Calendula officinalis*), jojoba oil (*Simmonsis chinensis*), mango oil (*Mangifera indica*), avocado oil (*Persea gratissima*), and/or mixtures thereof, among others.

Likewise, in another particular embodiment, agents stimulating healing, coadjuvant healing agents, agents stimulating re-epithelialization and/or coadjuvant re-epithelialization agents which can be contained in the liposomes in this invention are selected, for example and not restricted to, from the group formed by extracts of *Aristolochia clematis, Centella asiatica, Rosa moschata, Echinacea angustifolia, Symphytum officinale, Equisetum arvense, Hypericum perforatum, Mimosa tenuiflora, Persea gratisima, Prunus africana, Tormentilla erectea, Aloe vera*, Polyplant® Epithelizing [INCI: *Calendula Officinalis, Hypericum Perforatum, Chamomilla Recutita, Rosmarinus Officinalis*] marketed by Provital, Cytokinol® LS 9028 [INCI: Hydrolyzed Casein, Hydrolyzed Yeast Protein, Lysine HCl] marketed by Laboratories Serobiologiques/Cognis or Deliner® [INCI: *Zea May* (Corn) Kernel Extract] marketed by Coletica/Engelhard/BASF, allantoin, cadherins, integrins, selectins, hyaluronic acid receptors, immunoglobulins, fibroblast growth factor, connective tissue growth factor, platelet-derived growth factor, vascular endothelial growth factor, epidermal growth factor, insulin-like growth factor, keratinocyte growth factors, colony-stimulating factors, transforming growth factor beta, tumor necrosis factors, interferons, interleukins, matrix metalloproteinases, receptor protein tyrosine phosphatases, Antarcticine® [INCI: *Pseudoalteromonas* Ferment Extract], Decorinyl® [INCI: Tripeptide-10 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], acetyl-glutamyl-methionyl-alanyl-isoleucine, acetyl-arginyl-phenylglycyl-phenylglycine or acetyl-arginyl-6-aminohexanoyl-alanine marketed by Lipotec, among others.

In a particular embodiment, the agent stimulating the synthesis of dermal or epidermal macromolecules which can be contained in the liposomes of this invention is selected, for example and not restricted to, from the group formed by agents stimulating collagen synthesis, agents stimulating elastin synthesis, agents stimulating decorin synthesis, agents stimulating laminin synthesis, agents stimulating chaperone synthesis, agents stimulating hyaluronic acid synthesis, agents stimulating aquaporin synthesis, agents stimulating fibronectin synthesis, agents inhibiting collagen degradation, agents inhibiting elastin degradation, agents inhibiting serine proteases such as leukocyte elastase or cathepsin G, agents stimulating fibroblast proliferation, agents stimulating adipocyte proliferation, agents stimulating adipocyte differentiation, agents stimulating angiogenesis, agents stimulating glycosaminoglycan synthesis, DNA repair agents and/or DNA protecting agents, for example and not restricted to, extracts of *Centella asiatica, Saccharomyces cerevisiae, Solanum tuberosum, Rosmarinus officinalis, Vaccinium angustifolium*, extract of the algae *Macrocystis pyrifera, Padina pavonica*, extract of the plants soy, malt, flax, sage, red clover, kakkon-to, white lupin, hazelnut extract, corn extract, yeast extract, extract of beech tree shoots, extract of leguminosae seeds, extract of plant hormones such as gibberellins, auxins or cytokinins among others, or extract of zooplankton Salina, the product of milk fermentation with *Lactobacillus Bulgaricus*, asiaticosides and derivatives thereof, vitamin C and derivatives thereof, cinnamic acid and derivatives thereof, Matrixyl® [INCI: Palmitoyl Pentapeptide-3], Matrixyl® 3000 [INCI: Palmitoyl Tetrapeptide-3, Palmitoyl Oligopeptide] or Biopeptide CL™ [INCI: Glyceryl Polymethacrylate, Propylene Glycol, Palmitoyl Oligopeptide] marketed by Sederma, Antarcticine® [INCI: *Pseudomonas* Ferment Extract], Decorinyl® [INCI: Tripeptide-10 Citrulline], Serilesine® [INCI: hexapeptide-10], Lipeptide [INCI: Hydrolized vegetable protein], Aldenine® [INCI: Hydrolized Wheat Protein, Hydrolized Soy Protein, Tripeptide-1], Peptide AC29 [INCI: Acetyl Tripeptide-30 Citrulline], acetyl-arginyl-phenylglycyl-tryptophyl-phenylglycine, acetyl-arginyl-phenylglycyl-valyl-glycine or acetyl-arginyl-phenylglycyl-valyl-phenylglycine marketed by Lipotec, Drieline® PF [INCI: Yeast Betaglucan] marketed by Alban Muller, Phytovityl C® [INCI: Aqua, *Zea Mays* Extract] marketed by Solabia, Collalift® [INCI: Hydrolyzed Malt Extract] marketed by Coletica/Engelhard, Phytocohesine® PSP [proposed INCI: Sodium Beta-Sitosterol Sulfate] marketed by Seporga, minerals such as calcium among others, retinoids and derivatives thereof, isoflavonoids, carotenoids, in particular lycopene, pseudodipeptides, retinoids and derivatives thereof such as retinol or retinol palmitate among others, or heparinoids among others.

In a particular embodiment, the elastase inhibiting agent which can be contained in the liposomes of this invention is selected, for example and not restricted to, from the group formed by Elhibin® [INCI: *Glycine Soja* (Soybean) Protein], Preregen® [INCI: *Glycine Soja* (soybean) Protein, Oxido Reductases] or Regu®-Age [INCI: Hydrolyzed Rice Bran Protein, *Glycine Soja* (Soybean) Protein, Oxido Reductases] marketed by Pentapharm/DSM, Juvenesce [INCI: Ethoxydiglicol and caprylic Triglycerid, Retinol, Ursolic Acid, Phytonadione, Ilomastat], Micromerol™ [INCI: *Pyrus Malus* Extract], Heather Extract [INCI: *Calluna Vulgaris* Extract], Extracellium® [INCI: Hydrolyzed Potato Protein] or Flavagrum™ PEG [INCI: PEG-6 Isostearate, Hesperetin Laurate] marketed by Coletica/Engelhard/BASF, Proteasyl® TP LS8657 [INCI: *Pisum Sativum* Extract] marketed by Laboratoires Sérobiologiques/Cognis, acetyl-arginyl-phenylglycyl-tryptophyl-phenylglycine, acetyl-arginyl-phenylglycyl-valyl-glycine or acetyl-arginyl-phenylglycyl-valyl-phenylglycine marketed by Lipotec, Sepilift DPHP [INCI: Dipalmitoyl hydroxyproline] marketed by SEPPIC, Vitaderm® [INCI: Alcohol, Water, Glycerin, Hydrolyzed Rice Protein, *Ilex Aquifolium* Extract, Sodium Ursolate, Sodium Oleanolate] marketed by Rahn, Gatuline® Age Defense 2 [INCI: *Juglans Regia* (Walnut) Seed Extract] marketed by Gattefosse, IP 2000 [INCI: Dextran, Trifluoroacetyl Tripeptide-2] marketed by IEB and Atrium, Radicaptol [INCI: Propylene Glycol, Water, *Passiflora Incarnata* Flower Extract, *Ribes Nigrum* (Blackcurrant) Leaf Extract, *Vitis Vinifera* (grape) Leaf Extract] marketed by Solabia or ViaPure™ Boswellia [INCI: Olivanum (*Boswellia Serrata*) Extract] marketed by Soliance, among others.

In a particular embodiment, the matrix metalloproteinase inhibiting agent which can be contained in the liposomes of this invention is selected, for example and not restricted to, from the group formed by ursolic acid, isoflavones such as genistein, quercetin, carotenoids, lycopene, soy extract, cranberry extract, rosemary extract, *Trifolium pratense* (red clover) extract, *Phormium tenax* (New Zealand flax) extract, kakkon-to extract, sage extract, retinol and derivatives thereof, retinoic acid and derivatives thereof, sapogenins such as diosgenin, hecogenin, smilagenin, sarsapogenin, tigogenin, yamogenin and yucagenin among others, Collalift® [INCI: Hydrolyzed Malt Extract], Juvenesce [INCI: Ethoxydiglicol and Caprylic Triglyceride, Retinol, Ursolic Acid, Phytonadione, Ilomastat] or EquiStat [INCI *Pyrus Malus* Fruit Extract, *Glycine Soja* Seed Extract] marketed by Coletica/Engelhard, Pepha®-Timp [INCI: Human Oligopeptide-20], Regu-Age [INCI: Hydrolyzed Rice Bran Protein, *Glycine Soja* Protein, Oxido Reductases] or Colhibin [INCI: Hydrolyzed Rice Protein] marketed by Pentapharm, Lipeptide [INCI: Hydrolized vegetable protein] or Peptide AC29 [INCI: Acetyl Tripeptide-30 Citrulline] marketed by Lipotec, Litchiderm™ [INCI: *Litchi Chinensis* pericarp extract] or Arganyl™ [INCI: *Argania Spinosa* Leaf Extract] marketed by Laboratories Sérobiologiques/Cognis, MDI Complex® [INCI: glycosaminoglycans] or ECM-Protect® [INCI: Water (Aqua), Dextran, Tripeptide-2] marketed by Atrium Innovations, Dakaline [INCI: *Prunus amygdalus* dulcis, *Anogeissus leiocarpus* bark extract] marketed by Soliance, Homeostatine [INCI: *Enteromorpha compressa, Caesalpinia Spinosa*] marketed by Provital, Timp-Peptide [proposed INCI: Acetyl Hexapeptide] or ECM Moduline [proposed INCI: Palmitoyltripeptide] marketed by Infinitec Activos, IP2000 [INCI: Dextran, Trifluoroacetyl tripeptide-2] marketed by Institut Europeen de Biologie Cellulaire, Actimp 1.9.3® [INCI: Hydrolyzed Lupine Protein] marketed by Expanscience Laboratories, Vitaderm® [INCI: Alcohol, Water (Aqua), Glycerin, Hydrolyzed Rice Protein, *Ilex Aquifolium* Extract, Sodium Ursolate, Sodium Oleanolate] marketed by Rahn, adapalene, tetracyclines and derivatives thereof such as minocycline, rolitetracycline, chlortetracycline, metacycline, oxytetracycline, doxycycline, demeclocycline and their salts, Batimastat [BB94; [4-(N-hydroxyamino)-2R-isobutyl-3S-(thiophene-2-ylthiomethyl) succinyl]-L-phenylalanine-N-methylamide], Marimastat [BB2516; [2S-[N4(R*),2R*,3S]]-N4[2,2-dimethyl-1-[methylaminocarbonyl]propyl]-N1,2-dihydroxy-3-(2-methylpropyl)butanediamide], among others.

In a particular embodiment, the firming and/or redensifying and/or restructuring agent which can be contained in the liposomes of this invention is selected, for example and not restricted to, from the group formed by extracts of *Malpighia punicitolia, Cynara scolymus, Gossypium herbaceum, Aloe Barbadensis, Panicum miliaceum, Morns nigra, Sesamum indicum, Glycine soja, Triticum vulgare,* Pronalen® Refirming HSC [INCI: *Triticum vulgare, Silybum Marianum, Glycine Soy, Equisetum Arvense, Alchemilla Vulgaris, Medicago Sativa, Raphanus Sativus*] or Polyplant® Refirming [INCI: Coneflower, Asiatic *Centella, Fucus*, Fenugreek] marketed by Provital, Lanablue® [INCI: Sorbitol, Algae Extract] marketed by Atrium Innovations, Pepha®-Nutrix [INCI: Natural Nutrition Factor] marketed by Pentapharm, or vegetable extracts which contain isoflavones, Biopeptide EL™ [INCI: Palmitoyl Oligopeptide], Biopeptide CL™ [INCI: Palmitoyl Oligopeptide], Vexel® [INCI: Water (Aqua), Propylene Glycol, Lecithin, Caffeine, Palmitoyl Carnitine], Matrixyl® [INCI: Palmitoyl Pentapeptide-3], Matrixyl® 3000 [INCI: Palmitoyl Tetrapeptide-3, Palmitoyl Oligopeptide] or Bio-Bustyl™ [INCI: Glyceryl Polymethacrylate, Rahnella Soy Protein Ferment, Water (Aqua), Propylene Glycol, Glycerin, PEG-8, Palmitoyl Oligopeptide] marketed by Sederma, Dermosaccharides® HC [INCI: Glycerin, Water (Aqua), Glycosaminoglycans, Glycogen], Aglycal® [INCI: Mannitol, Cyclodextrin, Glycogen, *Aratostaphylos Uva Ursi* Leaf Extract], Cytokinol® LS [INCI: Hydrolyzed Casein, Hydrolyzed Yeast Protein, Lysine HCL] or Firmiderm® LS9120 [INCI: *Terminalia Catappa* Leaf extract, *Sambucus Negra* Flower Extract, PVP, Tannic Acid] marketed by Laboratoires Serobiologiques/Cognis, Liftline® [INCI: Hydrolyzed wheat protein], Raffermine® [INCI: Hydrolyzed Soy Flour] or Ridulisse C® [Hydrolyzed Soy Protein] marketed by Silab, Serilesine® [INCI: hexapeptide-10], Decorinyl™ [INCI: Tripeptide-10 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], marketed by Lipotec, Ursolisome® [INCI: Lecithin, Ursolic Acid, Atelocollagen, Xanthan Gum, Sodium Chondroitin Sulfate] or Collalift® [INCI: Hydrolyzed Malt Extract] marketed by Coletica/Engelhard, Syn®-Coll [INCI: Palmitoyl Tripeptide-5] marketed by Pentapharm, Hydriame® [INCI: Water (Aqua), Glycosaminoglycans, Sclerotium Gum] marketed by Atrium Innovations or IP2000 [INCI: Dextran, Trifluoroacetyl tripeptide-2] marketed by Institut Europeen de Biologie Cellulaire among others.

In a particular embodiment, the anti-glycation agent which can be contained in the liposomes of this invention is selected, for example and not restricted to, from the group formed by *Vaccinium angustifolium* extracts, ergothioneine and derivatives thereof, lysine, Aldenine® [INCI: Hydrolized Wheat Protein, Hydrolized Soy Protein, Tripeptide-1], Vilastene™ [INCI: Lysine HCl, Lecithin, Tripeptide-10 Citrulline], dGlyage™ [INCI: Lysine HCl, Lecithin, Tripeptide-9 Citrulline] or Eyeseryl® [INCI: Acetyl Tetrapeptide-5] marketed by Lipotec, hydroxystilbenes and derivatives thereof, resveratrol or 3,3',5,5'-tetrahydroxystilbene among others.

In a particular embodiment, the free radical scavenger and/or anti-atmospheric pollution agent, reactive carbonyl species scavenger which can be contained in the liposomes of this invention is selected, for example and not restricted to, from the group formed by tea extract, olive leaf extract, *Rosmarinus officinalis* extract or *Eichhornia crassipes* extract, benzopyrenes, vitamin C and derivatives thereof, vitamin E and derivatives thereof, in particular tocopherol acetate, ascorbyl glycoside, phenols and polyphenols, in particular tannins, tannic acid and ellagic acid, gallocatechol, anthocyanins, chlorogenic acid, stilbenes, indoles, cysteine-containing amino acid derivatives, in particular N-acetylcysteine, ergothioneine, S-carboxymethylcysteine, chelating agents, in particular EDTA or ethylenediamines, carotenoids, bioflavonoids, ubiquinone, idebenone, catalase, superoxide dismutase, lactoperoxidase, glutathione peroxidase, glutathione, benzylidene camphor, pidolates, lignans, melatonin, oryzanol, carnosine and derivatives thereof, GHK [INCI: Tripeptide-1] and its salts and/or derivatives, Aldenine® [INCI: Hydrolized wheat protein, hydrolized soy protein, tripeptide-1], Preventhelia™ [INCI: Diaminopropionoyl Tripeptide-33] or Lipochroman-6 [INCI: Dimethylmethoxy Chromanol] marketed by Lipotec, among others.

In a particular embodiment, the 5α-reductase inhibiting agent which can be contained in the liposomes of this invention is selected, for example and not restricted to, from the group formed by extract of *Cinnamommum zeylanicum, Laminaria saccharina, Spiraea ulmaria,* Nettle Root, *Pygeum africanum, Avena Sativa, Serenoa repens,* extracts of the plants *Arnica montana, Cinchona succirubra, Eugenia caryophyllata, Humulus lupulus, Hypericum perforatum, Mentha piperita, Rosmarinus officinalis, Salvia officinalis, Thymus vulgaricus,* extract of plants of the genus *Silybum,* extract of plants which contain sapogenins and in particular extract of plants of the genus *Dioscorea,* retinoids and in particular retinol, sulfur and derivatives thereof, zinc salts and in particular zinc lactate, gluconate, pidolate, carboxylate, salicylate or cysteate, selenium chloride, vitamin B6, pyridoxine, caproyl glycine, sarcosine, finasteride, dutasteride, izonsteride, turosteride and their salts, among others.

Likewise, in another particular embodiment, the lysyl- and/or prolyl-hydroxylase-inhibiting agent which may be contained in the liposomes of this invention is selected, for example and not restricted to, from the group formed by 2,4-diaminopyrimidine 3-oxide or 2,4-diamino-6-piperidinopyrimidine 3-oxide, among others.

In another particular embodiment, the defensin synthesis stimulating agent which can be contained in the liposomes of this invention is selected, for example and not restricted to, from the group formed by extracts of or hydrolyzed *Aloe Vera*, *Roast amaranth*, *Rehmannias radix*, *arnica*, *gardenia*, carrot, orange, peach, pineapple, mint, gentian, *hibiscus* flower, walnut tree leaf, calabaza, peony, *quinoa*, boldo, rough bindweed, sunflower, elderberry, seaweed, hydrolyzed corn, hydrolyzed soy, hydrolyzed rice, valine and its isomers and derivatives, calcium and its salts, α-MSH and fragments contained in the amino acid sequence of α-MSH, vitamin A and its derivatives and precursors, vitamin D3 and its derivatives, jasmonic acid, fumaric acid, malic acid, citric acid, ascorbic acid, lactic acid, acetic acid, adepic acid, tartaric acid, cinnamic acid, glutamic acid, succinic acid, inulin, alkyl glucosides, poly-D-glutamic acid, glycine, L-methionine, L-alanine, L-citrulline, lactoprotein, casein, lactoperoxidase, lysozyme, polyphenol, alkyl glucosides, *Lactobacillus* extract, *fusobacteria* extracts or non-photosynthetic and unfruitful filamentous bacteria, acetyl-glutamyl-methionyl-alanyl-isoleucine, acetyl-arginyl-phenylglycyl-phenylglycine or acetyl-arginyl-6-aminohexanoyl-alanine marketed by Lipotec, among others.

In another particular embodiment, the bactericidal and/or bacteriostatic agent and/or antimicrobial and/or germicidal agent and/or fungicidal agent and/or fungistatic agent and/or germ inhibitor which can be contained in the liposomes of this invention is selected, for example and not restricted to, from the group formed by macrolides, pyranosides, calcium channel blockers, for example and not restricted to, cinnarizine and diltiazem; hormones, for example and not restricted to, estril, analogues thereof or thyroxine and/or its salts, caprylyl glycol, imidazolidinyl urea, methyl 4-hydroxybenzoate [INCI: methylparaben], ethyl 4-hydroxybenzoate [INCI: ethylparaben], propyl 4-hydroxybenzoate [INCI: propylparaben], butyl 4-hydroxybenzoate [INCI: butylparaben], isobutyl 4-hydroxybenzoate [INCI: isobutylparaben], 1,3-bis(hydroxymethyl)-5,5-dimethylimidazolidine-2,4-dione [INCI: DMDM Hydantoin], benzyl 4-hydroxybenzoate [INCI: benzylparaben], benzyl alcohol, dehydroacetic acid, benzoic acid, sorbic acid, salicylic acid, formic acid, propionic acid, 2-bromo-2-nitropropane-1,3-diol, 3-p-chlorophenoxy-1,2-propanodiol [INCI: chlorphenesin], dichlorobenzyl alcohol, iodopropynyl butylcarbamate, benzalkonium chloride, odor-absorbing fungicides such as zinc ricinoleate, cyclodextrins, benzethonium chloride, chlorhexidine, ethanol, propanol, 1,3-butanediol, 1,2-propylene glycol, undecylenic acid, dehydroacetic acid, N-methylmorpholine acetonitrile (MMA), isopropanol, methanol, 1,2-hexanediol, 1,2-octanediol, pentylene glycol, glycerin laurate, glycerin caprilate, glycerin caprate, benzoyl peroxide, chlorhexidine gluconate, triclosan and derivatives thereof, phenoxyethanol, terpinen-4-ol, α-terpineol, resorcinol, stiemycin, erythromycin, neomycin, clindamycin and their esters, tetracyclines, metronidazole, azelaic acid, tolnaftate, nystatin, clotrimazole, ketoconazole, derivatives of zinc such as zinc piritionate or trithionate, zinc oxide and zinc undecylenate, piroctone olamine, isothiazolinones, selenium sulfur, benzyl hemiformal, boric acid, sodium borate, 6,6-dibromo-4,4-dichloro-2,2'-methylenediphenol [INCI: bromochlorophene], 5-bromo-5-nitro-1,3-dioxane, tosylchloramide sodium [INCI: chloramine T], chloroacetamide, p-chlorom-cresol, 2-benzyl-4-chlorophenol [INCI: chlorophene], dimethyl oxazolidine, dodecyl dimethyl-2-phenoxyethyl ammonium bromide [INCI: domiphen bromide], 7-ethyl bicyclooxazolidine, hexetidine, glutaraldehyde, N-(4-chlorophenyl)-N-[4-chloro-3-(trifluoromethyl)phenyl]-urea [INCI: cloflucarban], 2-hydroxy-4-isopropyl-2,4,6-cycloheptatriene-1-one [INCI: Hinokitiol], isopropylmethylphenol, mercury salts, aluminum salts, nisin, phenoxyisopropanol, o-phenylphenol, 3-heptyl-2-[(3-heptyl-4-methyl-3H-thiazole-2-ylidene)methyl]-4-methylthiazole iodide [INCI: Quaternium-73], silver chloride, sodium iodide, thymol, undecylenic acid, diethylenetriaminepentaacetic acid, ethylenediaminetetraacetic acid and ethylenediaminetetraacetates, lactoperoxidase, glucose oxidase, lactoferrin, alkylaryl sulfonates, halogenated phenols, phenol mercury acetate and/or mixtures thereof, benzamidines, isothiazolines, derivatives of phthalimide, derivatives of pyridine, guanidines, quinolines, 1,2-dibromo-2,4-dicyanobutane, iodine-2-propylbutyl carbamate, iodine, tamed iodines, peroxo compounds, 4-chloro-3,5-dimethylphenol, 2,2'-methylene-bis(6-bromo-4-chlorophenol), 3-methyl-4-(1-methylethyl)phenol, 3-(4-chlorophenoxy)-1,2-propanediol, 3,4,4'-trichlorocarbanilide (TTC), thiamine essence, eugenol, farnesol, glycerin monolaurate, diglycerin monocaprinate, N-alkyl salicylic acid amides such as n-octyl salicylic acid amide or n-decyl salicylic acid amide, derivatives of halogenated xylene and cresol, such as p-chloro-meta-cresol or p-chloro-meta-xylene, extracts of *Allium sativum*, *Calendula officinalis*, *Chamomilla recutita*, *Echinacea Purpura*, *Hyssopus Officinalis*, *Melaleuca alternifolia* or tea tree oil, carnation essence, menthol and mint essence, among others.

Likewise, in another particular embodiment, the NO-synthase inhibiting agent which can be contained in the liposomes of this invention is selected, for example and not restricted to, from the group formed by extracts of the plants *Vitis vinifera*, *Olea europaea* or *Gingko biloba* among others.

In a particular embodiment, the desquamating agent and/or keratolytic agent and/or exfoliating agent which can be contained in the liposomes of this invention is selected, for example and not restricted to, from the group formed by hydroxy acids and derivatives thereof, β-hydroxyacids, in particular salicylic acid and derivatives thereof, or gentisic acid; α-hydroxyacids and its salts, such as glycolic acid, ammonium glycolate, lactic acid, 2-hydroxyoctanoic acid, α-hydroxycaprylic acid, mandelic acid, citric acid, malic acid or tartaric acid; α- and β-hydroxybutyric acids; polyhydroxy acids such as gluconic acid, glucuronic acid or saccharic acid; keto acids such as pyruvic acid, glyoxylic acid; pyrrolidinecarboxylic acid; cysteic acid and derivatives; aldobionic acids; azelaic acid and derivatives thereof such as azeloyl diglycinate; ascorbic acid and derivatives thereof such as 6-O-palmitoylascorbic acid, ascorbyl glucoside, dipalmitoylascorbic acid, magnesium salt of ascorbic acid-2-phosphate (MAP), sodium salt of ascorbic acid-2-phosphate (NAP), ascorbyl tetraisopalmitate (VCIP); nicotinic acid, its esters and nicotinamide (also called vitamin B3 or vitamin PP); nordihydroguaiaretic acid; urea; oligofucoses; cinnamic acid; derivatives of the jasmonic acid; hydroxystilbenes such as resveratrol; *Saccarum officinarum* extract; enzymes involved in desquamation or degradation of the corneodesmosomes, such as glycosidases, stratum corneum chymotryptic enzyme (SCCE) or other proteases such as trypsin, chymotrypsin, sutilain, papain or bromelain; chelating agents such as ethylenediaminetetraacetic acid (EDTA), aminosulfonic compounds such as 4-(2-hydroxyethyl)piperazine-1-ethanesulfonic acid (HEPES) or sodium methylglycine diacetate (TRILON® M marketed by BASF); derivatives of 2-oxothiazolidine-4-carboxylic acid (procysteine); derivatives of sugars such as O-octanoyl-6-D-maltose and N-acetylglucosamine; chestnut extract (*Castanea sativa*) such as that marketed by SILAB under the name Recoverine® [INCI: Water (Aqua), *Castanea Sativa* Seed Extract]; *opuntia* extract (*Opuntia ficus*-indica) such as that marketed by SILAB as Exfolactive® [INCI: Hydrolyzed *Opuntia Ficus* Indica Flower Extract]; or Phytosphingosine SLC® [INCI: Salicyloyl Phytosphingosine] marketed by Degussa/Evonik, Peel-Moist [INCI: Glycerin, Papain, Calcium Pantothenate, Xanthan Gum, Caprylyl Glycol, Urea, Magnesium Lactate, Ethylhexylglycerin, Potassium Lactate, Serine, Alanine, Proline, Magnesium Chloride, Sodium Citrate]; extract or combination of extracts of *Saphora japonica*, papaya, pineapple, squash or yam, and/or mixtures thereof.

In another particular embodiment, the anti-inflammatory agent and/or analgesic agent which can be contained in the liposomes of this invention, is selected, for example and not restricted to, from the group formed by madecassoside extract, *echinacea* extract, amaranth seed oil, sandal wood oil, peach tree leaf extract, extract of *Aloe vera, Arnica montana, Artemisia vulgaris, Asarum maximum, Calendula officinalis, Capsicum, Centipeda cunninghamii, Chamomilla recutita, Crinum asiaticum, Hamamelis virginiana, Harpagophytum procumbens, Hypericum perforatum, Lilium candidum, Malva sylvestris, Melaleuca alternifolia, Origanum majorana, Origanum vulgare, Prunus laurocerasus, Rosmarinus officialis, Salix alba, Silybum marianum, Tanacetum parthenium, Thymus vulgaris, Uncaria guianensis* or *Vaccinum myrtillus*, mometasone furoate, prednisolone, nonsteroidal antiinflammatories including cyclooxygenase or lipoxygenase inhibitors, benzydamine, acetylsalicylic acid, rosmarinic acid, ursolic acid, derivatives of glycyrrhizinate, α-bisabolol, azulene and analogues, sericoside, ruscogenin, escin, scoline, rutin and analogues, hydrocortisone, clobetasol, dexamethasone, prednisone, paracetamol, amoxiprin, benorilate, choline salicylate, faislamine, methyl salicylate, magnesium salicylate, salsalate, diclofenac, aceclofenac, acemetacin, bromfenac, etodolac, indomethacin, oxamethacin, proglumetacin, sulindac, tolmetin, ibuprofen, dexibuprofen, carprofen, fenbufen, fenoprofen, flurbiprofen, ketoprofen, dexketoprofen, ketorolac, loxoprofen, naproxen, miroprofen, oxaprozin, pranoprofen, tiaprofenic acid, suprofen, mefenamic acid, meclofenamate, meclofenamic acid, flufenamic acid, tolfenamic acid, nabumetone, phenylbutazone, azapropazone, clofezone, kebuzone, metamizole, mofebutazone, oxyphenbutazone, phenazone, sulfinpyrazone, piroxicam, lornoxicam, meloxicam, tenoxicam, celecoxib, etoricoxib, lumiracoxib, parecoxib, rofecoxib, valdecoxib, nimesulide, naproxcinod, fluproquazone or licofelone, omega-3 and omega-6 fatty acids, morphine, codeine, oxycodone, hydrocodone, diamorphine, pethidine, tramadol, bupenorphine, benzocaine, lidocaine, chloroprocaine, tetracaine, procaine, amitriptyline, carbamazepine, gabapentin, pregabalin, bisabolol, Neutrazen™ [INCI: Water, Butylene Glycol, Dextran, Palmitoyl Tripeptide-8] marketed by Atrium Innovations/Unipex Group, Meliprene® [INCI: Dextran, Acetyl Heptapeptide-1] marketed by Institut Europeen de Biologie Cellulaire/Unipex Group, Skinasensyl™ [INCI: Acetyl Tetrapeptide-15] or Anasensyl™ [INCI: Mannitol, Ammonium Glycyrrhizate, Caffeine, *Hippocastanum* (Horse Chestnut) Extract] marketed by Laboratoires Serobiologiques/Cognis, Calmosensine™ [INCI: Acetyl Dipeptide-1] marketed by Sederma, coenzyme Q10 or alkylglycerine ethers.

In addition, in another particular embodiment, the whitening or depigmenting agent of the skin which can be contained in the liposomes of this invention is selected, for example and not restricted to, from the group formed by extracts of *Achillea millefolium, Aloe vera, Aradirachta indica, Asmuna japonica, Autocarpus incisus, Bidens pilosa, Broussonetia papyrifera, Chlorella vulgaris, Cimicifuga racemosa, Emblica officinalis, Glycyrrhiza glabra, Glycyrrhiza uralensis, Ilex purpurea, Ligusticum lucidum, Ligusticum wallichii, Mitracarpus scaber, Morinda citrifolia, Moms alba, Moms bombycis, Naringi crenulata, Prunus domesticus, Pseudostellariae radix, Rumex crispus, Rumex occidentalis, Sapindus mukurossi, Saxifragia sarmentosa, Scutellaria Galericulate, Sedum sarmentosum Bunge, Stellaria medica, Triticum Vulgare, Uva ursi* or *Whitania somnifera*, flavonoides, soy extract, lemon extract, orange extract, ginkgo extract, cucumber extract, geranium extract, gayuba extract, carob extract, cinnamon extract, marjoram extract, rosemary extract, clove extract, soluble liquorice extract or blackberry leaf extract, Lipochroman-6 [INCI: Dimethylmethoxy Chromanol] or Chromabright™ [INCI: Dimethylmethoxy Chromanyl Palmitate] marketed by Lipotec, Actiwhite™ LS9808 [INCI: Aqua, Glycerin, Sucrose Dilaurate, Polysorbate 20, *Pisum sativum* (Pea) extract] or Dermawhite® NF LS9410 [INCI: Mannitol, Arginine HCl, Phenylalanine, Disodium EDTA, Sodium Citrate, Kojic Acid, Citric Acid, Yeast Extract] marketed by Laboratoires Serobiologiques/Cognis, Lumiskin™ [INCI: Caprylic/Capric Triglycerid, Diacetyl-Boldine], Melaclear™ [INCI: Glycerin, Aqua, Dithiaoctanediol, Gluconic acid, Sutilains, Beta-carotene], O.D.A.white™ [INCI: octadecendioic acid] or Etioline™ [INCI: Glycerin, Butylene Glycol, *Arctostaphylos uva ursi* Leaf Extract, *Mitracarpus scaber* Extract] marketed by Sederma, Sepiwhite™ MSH [INCI: Undecylenoyl Phenylalanine] marketed by Seppic, Achromaxyl [INCI: Aqua, *Brassica napus* Extract] marketed by Vincience, Gigawhite™ [INCI: Aqua, Glycerin, *Malva sylvestris* (Mallow) Extract, *Mentha piperita* Leaf Extract, *Primula veris* Extract, *Alchemilla vulgaris* Extract, *Veronica officinalis* Extract, *Melissa officinalis* Leaf Extract, *Achillea millefolium* Extract], Melawhite® [INCI: Leukocyte Extract, AHA] or Melfade®-J [INCI: Aqua, *Arctostaphylos uva-ursi* Leaf Extract, Glycerin, Magnesium Ascorbyl Phosphate] marketed by Pentapharm, Albatin® [INCI: Aminoethylphosphoric Acid, Butylene Glycol, Aqua] marketed by Exsymol, Tyrostat™-11 [INCI: Aqua, Glycerin, *Rumex occidentalis* Extract] or Melanostatine®-5 [INCI: Dextran, Nonapeptide-1] marketed by Atrium Innovations, arbutin and its isomers, kojic acid and derivatives thereof, ascorbic acid and derivatives thereof such as 6-O-palmitoylascorbic acid, ascorbyl glucoside, dipalmitoylascorbic acid, magnesium salt of ascorbic acid-2-phosphate (MAP), sodium salt of ascorbic acid-2-phosphate (NAP), ascorbyl glucoside or ascorbyl tetraisopalmitate (VCIP); retinol and derivatives thereof including tretinoin and isotretinoin, idebenone, hydroxybenzoic acid and derivatives thereof, niacinamide, liquiritin, resorcinol and derivatives thereof, hydroquinone, α-tocopherol, γ-tocopherol, azelaic acid, azeloyl diglycinate, resveratrol, linoleic acid, α-lipoic acid, dihydrolipoic acid, α-hydroxy acids, β-hydroxy acids, ellagic acid, ferulic acid, cinnamic acid, oleanolic acid, aloesin and its derivatives and/or serine protease inhibitors, for example and not restricted to, tryptase, trypsin or PAR-2 inhibitors, among others.

In another particular embodiment, the melanin synthesis stimulating agent, propigmenting agent, self-tanning agent and/or melanocyte proliferation stimulating agent which can be contained in the liposomes of this invention is selected, for example and not restricted to, from the group formed by extracts of *Citrus Aurantium* Dulcis Fruit, *Coleus forskohlii, Coleus Esquirolii, Coleus Scutellariodes, Coleus Xanthanthus, Ballota nigra, Ballota lanata, Ballota suavelens, Mar-

*rubium cylleneum, Cistus creticus, Amphiachyris amoena, Aster oharai, Otostegia fruticosa, Plectranthus barbatus, Halimium viscosum* or *Larix laricema*, dihydroxyacetone and derivatives thereof, sugars, for example and not restricted to, melanin and derivatives thereof including melanin polymers and derivatives of melanin with a low molecular weight which are soluble in water, forskolin and derivatives thereof including deacetylforskolin and isoforskolin, tyrosine and derivatives thereof including acetyl tyrosine, oleoyl tyrosine, 3-amino tyrosine and 3-nitrotyrosine, copper salts such as CuC12, carotenoids, canthaxanthins, polymers of dihydroxyindole carboxylic acid, 3,4-dihydroxybenzoic acid, 3-amino-4-hydroxybenzoic acid, aloin, emodin, alizarin, dihydroxyphenylalanine, 4,5-dihydroxynaphthalene-2-sulfonic acid, 3-dimethylaminophenol or p-aminobenzoic acid, Melatime™ [INCI: Acetyl Tripeptide-40] marketed by Lipotec, Heliostatine IS™ [INCI: *Pisum Sativum* Extract] marketed by Vincience/ISP, Vegetan [INCI: Dihydroxyacetone] or Vegetan Premium [INCI: Dihydroxyacetone, Melanin] marketed by Soliance, MelanoBronze [INCI: *Vitex Agnus Castus* Extract, Acetyl Tyrosine] marketed by Mibelle Biochemistry, Melitane® [INCI: Acetyl Hexapeptide-1] marketed by Institut Europeen de Biologie Cellulaire/Unipex Innovations, Actibronze® [INCI: Hydrolyzed Wheat Protein, Acetyl Tyrosine, Copper Gluconate] or Instabronze® [INCI: Dihydroxyacetone, Tyrosine] marketed by Alban Muller, Thalitan [INCI: Hydrolyzed Algin, Magnesium Sulfate, Manganese Sulfate] marketed by CODIF, Tyrosilane® [INCI: Methylsilanol Acetyltyrosine] marketed by Exsymol, Tyr-Excel™ [INCI: Oleoyl Tyrosine, *Luffa Cylindrica* Seed Oil, Oleic Acid] or Tyr-O1 [INCI: Oleoyl Tyrosine, Butylene glycol, Oleic Acid] marketed by Sederma/Croda, Bronzing S.F. [proposed INCI: Butiryl Pentapeptide] marketed by Infinitec Activos or Biotanning® [INCI: Hydrolyzed *Citrus Aurantium* Dulcis Fruit Extract] marketed by Silab, among others.

In a particular embodiment, the anti-wrinkle and/or anti-aging agent which can be contained in the liposomes in this invention is selected, for example and not restricted to, from the group formed by extracts of *Vitis vinifera, Rosa canina, Curcuma longa, Iris pallida, Theobroma cacao, Ginkgo biloba, Leontopodium Alpinum* or *Dunaliella salina*, Matrixyl® [INCI: Palmitoyl Pentapeptide-4], Matrixyl 3000® [INCI: Palmitoyl Tetrapeptide-7, Palmitoyl Oligopeptide], Essenskin™ [INCI: calcium hydroxymethionine], Renovage [INCI: teprenone] or Dermaxyl® [INCI: Palmitoyl Oligopeptide] marketed by Sederma, Vialox® [INCI: Pentapeptide-3], Syn®-Ake® [INCI: Dipeptide Diaminobutyroyl Benzylamide Diacetate], Syn®-Coll [INCI: Palmitoyl Tripeptide-5], Phytaluronate [INCI: Locust Bean (*Ceratonia Siliqua*) Gum] or Preregen [INCI: *Glycine Soja* (Soybean) Protein, Oxido Reductases] marketed by Pentapharm/DSM, Myoxinol™ [INCI: Hydrolyzed *Hibiscus Esculentus* Extract], Syniorage™ [INCI: Acetyl Tetrapeptide-11], Dermican™ [INCI: Acetyl Tetrapeptide-9] or DN-AGE™ LS [INCI: *Cassia Alata* leaf Extract] marketed by Laboratoires Serobiologiques/Cognis, Algisum C® [INCI: Methylsilanol Mannuronate] or Hydroxyprolisilane CN® [INCI: Methylsilanol Hydroxyproline Aspartate] marketed by Exsymol, Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide-18], Aldenine® [INCI: Hydrolized wheat protein, hydrolized soy protein, Tripeptide-1], Preventhelia™ [INCI: Diaminopropionoyl Tripeptide-33], Decorinyl™ [INCI: Tripeptide-10 Citrulline], Trylagen® [INCI: *Pseudoalteromonas* Ferment Extract, Hydrolyzed Wheat Protein, Hydrolyzed Soy Protein, Tripeptide-10 Citrulline, Tripeptide-1], Eyeseryl® [INCI: Acetyl Tetrapeptide-5], Peptide AC29 [INCI: Acetyl Tripeptide-30 Citrulline], Lipochroman-6 [INCI: Dimethylmethoxy Chromanol], Chromabright™ [INCI: Dimethylmethoxy Chromanyl Palmitate], Antarcticine® [INCI: *Pseudoalteromonas* Ferment Extract], Vilastene™ [INCI: Lysine HCl, Lecithin, Tripeptide-10 Citrulline], dGlyage™ [INCI: Lysine HCl, Lecithin, Tripeptide-9 Citrulline], acetyl-arginyl-phenylglycyl-tryptophyl-phenylglycine, acetyl-arginyl-phenylglycyl-valyl-glycine or acetyl-arginyl-phenylglycyl-valyl-phenylglycine, Inyline™ [INCI: Acetyl Hexapeptide-30] marketed by Lipotec, Kollaren® [INCI: Tripeptide-1, Dextran] marketed by Institut Europeen de Biologie Cellulaire, Collaxyl® IS [INCI: Hexapeptide-9], Laminixyl IS™ [INCI: Heptapeptide], Orsirtine™ GL [INCI: *Oryza Sativa* (Rice) Extract], D'Orientine™ IS [INCI: *Phoenix Dactylifera* (Date) Seed Extract], Phytoquintescine™ [INCI: Einkorn (*Triticum Monococcum*) Extract] or Quintescine™ IS [INCI: Dipeptide-4] marketed by Vincience/ISP, BONT-L-Peptide [INCI: Palmitoyl Hexapeptide-19] marketed by Infinitec Activos, Deepaline™ PVB [INCI: Palmitoyl hydrolyzed Wheat Protein] or Sepilift® DPHP [INCI: Dipalmitoyl Hydroxyproline] marketed by Seppic, Gatuline® Expression [INCI: *Acmella oleracea* Extract], Gatuline® In-Tense [INCI: *Spilanthes Acmella* Flower Extract] or Gatuline® Age Defense 2 [INCI: *Juglans Regia* (Walnut) Seed Extract] marketed by Gattefossé, Thalassine™ [INCI: Algae Extract] marketed by Biotechmarine, ChroNOline™ [INCI: Caprooyl Tetrapeptide-3] or Thymulen-4 [INCI: Acetyl Tetrapeptide-2] marketed by Atrium Innovations/Unipex Group, EquiStat [INCI: *Pyrus Malus* Fruit Extract, *Glycine Soja* Seed Extract] or Juvenesce [INCI: Ethoxydiglicol and Caprylic Triglycerid, Retinol, Ursolic Acid, Phytonadione, Ilomastat] marketed by Coletica, Ameliox [INCI: Carnosine, Tocopherol, *Silybum Marianum* Fruit Extract] or PhytoCellTec *Malus Domestica* [INCI: *Malus Domestica* Fruit Cell Culture] marketed by Mibelle Biochemistry, Bioxilift [INCI: *Pimpinella Anisum* Extract] or SMS Anti-Wrinkle® [INCI: *Annona Squamosa* Seed Extract] marketed by Silab, Ca2+ channel blockers, for example and not restricted to, alverin, manganese or magnesium salts, certain secondary or tertiary amines, retinol and derivatives thereof, resveratrol, idebenone, coenzyme Q10 and derivative thereof, boswellic acid and derivatives thereof, GHK and derivatives thereof and/or salts, carnosine and derivatives thereof, DNA repair enzymes, for example and not restricted to, photolyase or T4 endonuclease V, or chloride channel blockers among others.

In a particular embodiment, the lipolytic agent or lipolysis stimulating agent, venotonic agent and/or anti-cellulite agent which can be contained in the liposomes of this invention is selected, for example and not restricted to, from the group formed by extracts of *Bupleurum Chinensis, Cecropia Obtusifolia, Celosia Cristata, Centella Asiatica, Chenopodium Quinoa, Chrysanthellum Indicum, Citrus Aurantium Amara, Coffea Arabica, Coleus Forskohlii, Commiphora Myrrha, Crithmum Maritimum, Eugenia Caryophyllus, Ginkgo Biloba, Hedera Helix* (ivy extract), *Hibiscus Sabdariffa, Ilex Paraguariensis, Laminaria Digitata, Nelumbium Speciosum, Paullinia Cupana, Peumus Boldus, Phyllacantha Fibrosa, Prunella Vulgaris, Prunus Amygdalus Dulcis, Ruscus Aculeatus* (Butcherbroom extract), *Sambucus Nigra, Spirulina Platensis* Algae, *Uncaria Tomentosa* or *Verbena Officinalis*, dihydromyricetin, coenzyme A, lipase, glaucine, esculin, visnadine, Regu®-Shape [INCI: Isomerized Linoleic Acid, Lecithin, Glycerin, Polysorbate 80] marketed by Pentapharm/DSM, UCPeptide™ V [INCI: Pentapeptide] or AT Peptide™ IS [INCI: Tripeptide-3] marketed by Vincience/ISP, Liporeductyl® [INCI: Caffeine, Butcherbroom (*Ruscus Aculeatus*) Root Extract, TEA-Hydroiodide, Carnitine, Ivy (*Hedera Helix*) Extract, Escin, Tripeptide-1] marketed by Lipotec, Adiposlim [INCI: Sorbitan Laurate, Lauroyl Proline] marketed by SEPPIC, caffeine, carnitine, escin and/or triethanolamine iodide, among others.

In a particular embodiment, the heat shock protein synthesis stimulating agent which can be contained in the liposomes of this invention is selected, for example and not restricted to, from the group formed by extracts of *Opuntia ficus* indica, *Salix alba, Lupinus* spp., *Secale cereale*, extracts of red algae from the *Porphyra* genus, extracts of crustaceans from the *Artemia* genus, jojoba seed oil, grape seed extracts, green tea extracts, geranylgeranylacetone, celastrol, zinc and its salts, 2-cyclopenten-1-one, proteasome inhibitors, for example and not restricted to, bortezomib; prostaglandins and derivatives thereof, hydroxylamine and derivatives thereof, for example and not restricted to, bimoclomol; chalcone and derivatives thereof, hyperosmotic agents, for example and not restricted to, sorbitol and derivatives thereof, mannitol and derivatives thereof or glycerol and derivatives thereof, isosorbide, urea or salicylic acid and derivatives thereof among others, or mixtures thereof.

In a particular embodiment, the hair growth inducing or hair loss retardant agent which can be contained in the liposomes of this invention is selected, for example and not restricted to, from the group formed by the extracts of *Tussilago farfara* or *Achillea millefolium*, nicotinic acid esters such as C3-C6 alkyl nicotinates such as methyl or hexyl nicotinate, benzyl nicotinate, or tocopheryl nicotinate; biotin, 5α-reductase-inhibiting agents, anti-inflammatory agents, retinoids, for example and not restricted to, All-trans-retinoic acid or tretinoin, isotretinoin, retinol or vitamin A, and derivatives thereof, such as acetate, palmitate, propionate, motretinide, etretinate and zinc salt of trans-retinoic acid; anti-bacterial agents, calcium channel blockers, for example and not restricted to, cinnarizine and diltiazem; hormones, for example and not restricted to, estriol, its analogues or thyroxine, its analogues and/or salts; antiandrogenic agents, for example and not restricted to, oxendolone, spironolactone or diethylstilbestrol; anti-radical agents, esterified oligosaccharides, for example and not restricted to, those described in documents EP 0211610 and EP 0064012; derivatives of hexasaccharide acids, for example and not restricted to, glucose-saccharide acid or those described in document EP 0375388; glucosidase inhibitors, for example and not restricted to, D-glucaro-1,5-lactam or those described in document EP 0334586; glycosaminoglycanase and proteoglycanase inhibitors, for example and not restricted to, L-galactono-1,4-lactone or those described in document EP 0277428; tyrosine kinase inhibitors, for example and not restricted to, 1-amido-1-cyano(3,4-dihydroxyphenyl)ethylene or those described in document EP 0403238, diazoxides, for example and not restricted to, 7-(acetylthio)-4',5'-dihydrospiro [androst-4-ene-17,2'-(3H)furan]-3-one, 1,1-dioxide of 3-methyl-7-chloro[2H]-1,2,4-benzothiadiazine or spirooxazine; phospholipids, for example and not restricted to, lecithin; salicylic acid and derivatives thereof, hydroxycarboxylic or keto carboxylic acid and esters thereof, lactone and its salts; anthralin, eicose-5,8,11-trienoic acids and esters thereof or amides among others, minoxidil and derivatives thereof or mixtures thereof.

In another particular embodiment the body hair growth inhibiting or retardant agent which may be contained in the liposomes of this invention is selected, for example and not restricted to, from the group formed by activin or activin agonists, flavonoids such as quercetin, curcumin, galangin, fisetin, myricetin, apigenin; propyl gallate, nordihydroguaiaretic acid, caffeic acid, tyrosine kinase inhibitors such as lavendustin, erbstatin, tyrphostins, benzoquinone-ansamycin herbimycin A, thiazolidinediones, phenazocine, 2,3-dihydro-2-thioxo-1H-indol-3-alcanoic acids, phenothiazine derivatives such as thioridazine; sphingosine and derivatives thereof, staurosporine and derivatives thereof, glycyrrhetinic acid, lauryl isoquinolinium bromide, Decelerine™ [INCI: Lauryl Isoquinolium Bromide, *Pseudoalteromonas* Ferment Extract] marketed by Lipotec or serine protease inhibitors, trypsin and/or mixtures thereof.

In a particular embodiment, the cosmetic and/or absorbent and/or body odor masking deodorant and/or antiperspirant agent, perfuming substance and/or perfumed oil which can be contained in the liposomes of this invention is selected, for example and not restricted to, from the group formed by the complex salt of ricinoleic acid, Styrax, derivatives of abiotic acid, sage essence, chamomile essence, carnation essence, lemon balm essence, mint essence, cinnamon leaf essence, lime flower essence, juniper berry essence, vetiver essence, olibanum essence, galbanum essence, labdanum essence, lavender essence, peppermint essence, bergamot orange, dihydromyrcenol, lilial, lyral, citronellol, lemon essence, mandarin essence, orange essence, lavender essence, muscat, geranium bourbon essence, aniseed, cilantro, cumin, juniper, extracts of fleur-de-lis, lilac, roses, jasmin, bitter orange blossom; benzyl acetate, p-tert-butylcyclohexyl acetate, linalyl acetate, phenylethyl acetate, ethylmethylphenyl glycinate, linalyl benzoate, benzyl formate, allyl cyclohexyl propionate, styrallyl propionate, benzyl salicylate, benzyl ethyl ether, linear alkanes with from 8 to 18 carbon atoms, citral, ricinoleic acid, citronellal, citronelyl oxyacetaldehyde, cyclamen aldehyde, hydroxycitronellal, bourgeonal, ionones, methylethylketone, anethole, eugenol, isoeugenol, geraniol, linalool, terpineol, phenylethyl alcohol, α-hexylcinnamaldehyde, geraniol, benzylacetone, cyclamen aldehyde, Boisambrene Forte®, ambroxan, indole, hedione, sandelice, cyclovertal, β-damascone, allyl amyl glycolate, dihydromyrcenol, phenoxyethyl isobutyrate, cyclohexyl salicylate, Vertofix Coeur, Iso-E-Super, Fixolide NP, Evernyl, phenylacetic acid, geranyl acetate, romillat, irotyl, floramate, active astringent products such as aluminum chloride, aluminum chlorohydrate, aluminum dichlorohydrate, aluminum sesquichlorohydrate, aluminum hydroxyallantoinate, aluminum chlorotartrate, aluminum and zirconium trichlorohydrate, aluminum and zirconium tetrachlorohydrate, aluminum and zirconium pentachlorohydrate and/or mixtures thereof.

In a particular embodiment, the antioxidant which can be contained in the liposomes of this invention is selected, for example and not restricted to, from the group formed by butylhydroxyanisole, 2,6,-di-tert-butyl-4-methylphenol, propyl gallate, probucol, polyphenoles, ascorbic acid and its salts, enzymes such as catalase, superoxide dismutase and peroxidases; citric acid, citrates, monoglyceride esters, calcium metabisulfate, lactic acid, malic acid, succinic acid, tartaric acid, vitamin A or β-carotene, vitamins E and C, zinc, copper, mannitol, reduced glutathione, carotenoids such as cryptoxanthin, astaxanthin and lycopene; cysteine, uric acid, taurine, tyrosine, lutein, zeaxanthin, N-acetylcysteine, carnosine, γ-glutamylcysteine, quercetin, lactoferrin, dihydrolipoic acid, tea catechins, retinyl palmitate and derivatives thereof, bisulfate, metabisulfite and sodium sulfite, chromans, chromens and their analogues, Lipochroman-6 [INCI: Dimethylmethoxy Chromanol], chelating agents of metals such as EDTA, sorbitol, phosphoric acid or dGlyage™ [INCI: Lysine HCl, Lecithin, Tripeptide-9 Citrulline]; extract of *Ginkgo Biloba*, plant extracts such as sage, pomegranate, rosemary, oregano, ginger, marjoram, cranberry, grape, tomato, green tea or black tea; oleoresin extract, extract of plants which contain phenols such as vanillin, ellagic acid and resveratrol; tertiary butylhydroquinone or mixtures thereof, metal salts with a valence of 2 such as selenium, cadmium, vanadium or zinc; α-lipoic acid, coenzyme Q, idebenone or derivatives thereof.

In a particular embodiment, the agent inhibiting sweat-degrading enzymes which can be contained in the liposomes of this invention is selected, for example and not restricted to, form the group formed by trialkyl citrates such as trimethyl citrates, tripropyl citrate, triisopropyl citrate, tributyl citrate or triethyl citrate; lanosterine sulfate or phosphate, cholesterin, campesterin, stigmasterin and sitosterin; dicarboxylic acids and their esters, such as glutaric acid, monoethyl glutarate, diethyl glutarate, adipic acid, monoethyl adipate, diethyl adipate; malonic acid and diethyl malonate, hydroxycarboxylic acids and their esters such as malic acid, tartaric acid or diethyl tartrate, zinc glycinate and/or mixtures thereof.

In another particular embodiment, the agent capable of filtering UV rays which can be contained in the liposomes of this invention is selected, for example and not restricted to, from the group formed by organic or mineral photoprotective agents active against A and/or B rays such as substituted benzotriazoles, substituted diphenylacrylates, organic nickel complexes, umbelliferone, urocanic acid, biphenyl derivatives, stilbene, 3-benzylidene camphor, and derivatives thereof such as 3-(4-methylbenzylidene)camphor; derivatives of 4-aminobenzoic acid, 2-ethylhexyl 4-(dimethylamino)benzoate, 2-octyl 4-(dimethylamino)benzoate and amyl 4-(dimethylamino)benzoate; cinnamic acid esters, such as 2-ethylhexyl 4-methoxycinnamate or diethylamino hydroxybenzoyl hexyl benzoate, propyl 4-methoxycinnamate, isoamyl 4-methoxycinnamate, 2-ethylhexyl (octocrylenes) (2-cyano-3,3-phenyl cinnamate; salicylic acid esters, such as 2-ethylhexyl salicylate, 4-isopropylbenzyl salicylate, homomenthyl salicylate; benzophenone derivatives, such as 2-hydroxy-4-methoxybenzophenone, 2-hydroxy-4-methoxy-4'-methylbenzophenone, 2,2'-dihydroxy-4-methoxybenzophenone; benzylmalonic acid esters, such as di-2-ethylhexyl 4-methoxybenzalmalonate; triazine derivatives, such as 2,4,6-trianilino, p-carbo-2'-ethyl-1'-hexyloxy-1,3,5-triazine, octyl triazone or dioctyl butamido triazones; propane-1,3-diones, such as 1-(4-tert-butylphenyl)-3-(4'-methoxyphenyl)propane-1,3-dione; ketotricyclo (5.2.1.0)decane derivatives; 2-phenylbenzimidazole-5-sulfonic acid; benzophenone sulfonic acid derivatives, such as 2-hydroxy-4-methoxybenzophenone-5-sulfonic and its salts; 4-(2-oxo-3-bornylidenemethyl)benzenesulfonic acid, benzoyl methane derivatives, such as benzoyl methane 2-methyl-5-(2-oxo-3-bornylidene)sulfonic acid, such as 1-(4'-tert-butylphenyl)-3-(4'-methoxyphenyl)propane-1,3-dione, 4-tert-butyl-4'-methoxydibenzoylmethane, 1-phenyl-3-(4'-isopropylphenyl)-propane-1,3-dione, enamine compounds, anthranilates, silicons, benzimidazole derivatives, imidazolines, benzoyl derivatives, Chromabright™ [INCI: Dimethylmethoxy Chromanyl Palmitate] or Preventhelia™ [INCI: Diaminopropionoyl Tripeptide-33] both marketed by Lipotec, metal oxides such as zinc oxide, titanium, iron, zirconium, silicon, manganese, aluminum and cerium; silicates, talc, barium sulfate, zinc stearate, carbon nanotubes and/or mixtures thereof.

In addition, in another particular embodiment, the agent stimulating or regulating keratinocyte differentiation which can be contained in the liposomes of this invention is selected, for example and not restricted to, from the group formed by minerals such as calcium, retinoids such as retinol or tretinoin, analogues of vitamin D3 such as calcitriol, calcipotriol or tacalcitol, lupine (*Lupinus albus*) extract such as that marketed by SILAB under the name Structurin® [INCI: Hydrolyzed Lupine Protein], β-sitosterol sulfate, such as that marketed by Vincience/ISP with the name Phytocohesine PSP® [INCI: Sodium Beta-sitosterol Sulfate], maize (*Zea Mays*) extract such as that marketed by Solabia with the name Phytovityl C® [INCI: Water (Aqua), *Zea Mays* Extract], Helix Aspersa Muller glycoconjugates and/or mixtures thereof.

Likewise, in another particular embodiment, the muscle relaxant, agent inhibiting muscle contraction, agent inhibiting acetylcholine receptor clustering and/or anticholinergic agent which can be contained in the liposomes of this invention is selected, for example and not restricted to, from the group formed by extracts of *Atropa belladonna, Hyoscyamus niger, Mandragora officinarum, Chondodendron tomentosum*, plants of the *Brugmansia* genus, or the *Datura* genus, *Clostridium botulinum* toxin, peptides derived from the protein SNAP-25 or Inyline™ [INCI: Acetyl Hexapeptide-30] marketed by Lipotec, baclofen, carbidopa, levodopa, bromocriptine, chlorphenesin, chlorzoxazone, donepezil, mephenoxalone, reserpine, tetrabenazine, dantrolene, thiocolchicoside, tizanidine, clonidine, procyclidine, glycopyrrolate, atropine, hyoscyamine, benztropine, scopolamine, promethazine, diphenhydramine, dimenhydrinate, dicyclomine, cyclobenzaprine, orphenadrine, flavoxate, cyclopentolate, ipratropium, oxybutynin, pirenzepine, tiotropium, trihexyphenidyl, tolterodine, tropicamide, solifenacin, darifenacin, mebeverine, trimethaphan, atracurium, cisatracurium, doxacurium, fazadinium, metocurine, mivacurium, pancuronium, pipecuronium, rapacuronium, tubocuranine, dimethyl tubocuranine, rocuronium, vecuronium, suxamethonium, 18-methoxycoronaridine, carisoprodol, febarbamate, meprobamate, metocarbamol, phenprobamate, tibamate, anticonvulsant agents such as levetiracetam, stiripentol, phenobarbital, methylphenobarbital, pentobarbital, metharbital, barbexaclone, pirimidone, carbamazepine, oxcarbazepine, benzodiazepines, for example and not restricted to, clonazepam, cloxazolam, clorazepate, diazepam, flutoprazepam, lorazepam, midazolam, nitrazepam, nimetazepam, phenazepam, temazepam, tetrazepam or clobazam, among others.

The liposomes of this invention can be a final composition on their own, available for application without having to carry out any kind of concentration, solution, dilution, dispersion, pulverization, spraying procedure or any other similar procedure known by the person skilled in the art, or an intermediate composition to which one or several of the previous procedures will be carried out or any other procedure known by the person skilled in the art with the aim of obtaining a composition, wherein this composition is a final composition.

A second aspect of this invention relates to the use of liposomes which contain active ingredients and/or cosmetic and/or dermopharmaceutical adjuvants for the treatment of textile materials, and which are bound to cationic polymers, wherein these polymers, when they come into contact with textile material form a network on the surface of the textile material.

Another aspect of this invention relates to compositions which comprise liposomes that contain active ingredients and/or cosmetic and/or dermopharmaceutical adjuvants, and which are bound to cationic polymers, wherein these polymers, when they come into contact with textile material form a network on the surface of the textile material.

The composition which comprises the liposomes of this invention is used for the treatment of textile materials and can be presented in liquid form, such as washing agents, sprays, liquid soap or gels, or also in solid form, such as powder, granules or compact products. In addition, these compositions contain other components, for example and not restricted to, surfactants, agents which increase percutaneous absorption, agents for the prior treatment of textile materials, agents for the treatment of marks, abrasives, water softeners, fabric softeners, solvents or solubilizing agents, agents for the variation of touch and finish, dirt-repelling agents, antistatic agents, enzymes, agents which aid ironing, color and/or colorant brightening agents, shine agents, optical clearing agents, graying inhibitors or compounds for the loosening of dirt, color transfer inhibitors, phobizing and impregnating agents, swelling or thickening agents, consistency-generating agents, silicon agents, agents which increase the percutaneous absorption of liposomes, whitening agents and textile material bleaching activators, hydrophilization agents or mixtures thereof.

In another particular embodiment, the surfactant which can be contained in the composition is selected from among the surfactants mentioned above which form mixed liposomes. Preferably, the surfactant in the composition is an anionic surfactant, and more preferably it is selected from the group formed by sulfonates such as alkylbenzene sulfonates, alkylnaphthalene sulfonates, ethoxylated fatty acid sulfonates, aliphatic sulfonates, hydroxyalkane sulfonates, alkyl glyceryl ether sulfonates, perfluorooctane sulfonate; alkyl sulfosuccinates, alkyl sulfoacetates, alkyl sulfates such as sodium and ammonium lauryl sulfate, ethoxylated alkyl sulfates, fatty ester sulfates, ethoxylated fatty alcohol sulfates, alkyl ether sulfates, acyl isocyanates, pentafluoro octanoates, carboxylates, ethoxylated alkylphenols, ethanolammonium, diethanolammonium, methylammonium, dimethylammonium, trimethylammonium salts; alkyl taurates, acyl or fatty acids; alkyl or acyl sarcosinates, phosphates such as phosphate esters, alkyl phosphates, lauryl ether polyoxyethylene phosphate, glutamates and stearates. The composition is preferably a washing agent or a spray.

In another particular embodiment, the agent which increases the percutaneous absorption of the liposomes contained in the composition is selected, for example and not restricted to, from the group formed by dimethyl sulfoxide, dimethylacetamide, dimethylformamide, surfactants, azona (1-dodecylazacycloheptan-2-one), alcohol, urea, ethoxydiglycol, acetone, propylene glycol or polyethylene glycol among others. Preferably, the composition is a washing agent or a spray.

In another particular embodiment, the touch and finish variation agent or dirt-repelling agent which can be contained in the composition is selected, for example and not restricted to, from the group formed by terephthalates and fluorine compounds. Preferably, the composition is a washing agent or a spray.

In another particular embodiment, the water softening agent which can be contained in the composition is selected from the group formed by zeolites, montmorillonite, silicates, aluminosilicates, alkali metal polyphosphates such as sodium hexametaphosphate, tetrasodium pyrophosphate or sodium tripolyphosphate; monosodium phosphate, disodium phosphate, trisodium phosphate; ethylenediamine derivatives such as EDTA; nitriloacetic acid, alkali salts such as carbonate and sodium bicarbonate; ammonium acetate, sodium propionate, acrylic acid and polyacrylate polymers, inorganic peroxides such as percarbonate or perborate; citric acid and its salts, malic acid, sulfonic acid, gluconic acid, phosphonic acid, tetraacetic acid and/or mixtures thereof. Preferably, the composition is a washing agent or a spray.

In another particular embodiment, the agent which aids ironing which can be contained in the composition is selected from the group formed by silicone oils or synthetic hydrocarbons. Preferably, the silicone is selected, for example and not restricted to, from the group formed by polydimethylsiloxanes, poly methyl phenyl siloxanes, simethicones, cyclic silicones, compounds of silicone modified with amine groups, fatty acids, alcohol, polyether, epoxy, fluorine, glycoside and/or alkyl. Preferably, the composition is a washing agent or a spray.

In another particular embodiment, the optical clearing agent ironing which can be contained in the composition is selected, for example and not restricted to, from the group formed by derivatives of diaminostilbene disulfonic acid, such as 4,4'-bis(2-aniline-4-morpholine-1,3,5-triazinyl-6-amino)stilbene-2,2'-disulfonic acid salts, substituted diphenyl stirenes, such as 4,4'-bis(2-sulfostyryl)-diphenyl alkali salts, 4,4'-bis(4-chloro-3-sulfostyryl)-diphenyl, or 4-(4-chlorostyryl)-4'-(2-sulfostyryl)-diphenyl and/or mixtures thereof. The composition is preferably a washing agent or a spray.

In another particular embodiment, the graying inhibitor or the compound for the loosening of dirt which can be contained in the composition is selected, for example and not restricted to, from the group formed by hidrosoluble colloids, such as cola, gelatin, ether carboxylic acid salts, ether sulfonic acids of starch or cellulose, sulfate salt acids of cellulose or starch, hydrosoluble polyamides which contain acid groups, aldehyde starches, cellulose ethers such as carboxymethylcellulose, methylcellulose, hydroxyalkylcellulose, methylhydroxyethylcellulose, methylhydroxypropylcellulose, methylcarboxymethylcellulose and mixtures thereof. The composition is preferably a washing agent or a spray.

In another particular embodiment, the phobizing and impregnating agent which can be contained in the composition is selected, for example and not restricted to, from the group formed by starch derivatives for the stiffening of textile materials. The composition is preferably a washing agent or a spray.

Likewise, in another particular embodiment, the enzyme which can be contained in the composition is selected from the group formed by oxidases, proteases, lipases, cutinases, amylases, pullulanases, cellulases, hemicellulases, xylanases and peroxidases, for example and not restricted to, active enzymatic products obtained from fungi or bacteria, such as *Bacillus subtilis, Bacillus licheniformis, Streptomyces griseus, Humicola lanuginosa, Humicola insolens, Pseudomonas pseudoalcaligenes* or *Pseudomonas cepacia*, among others. The composition is preferably a washing agent or a spray.

In another particular embodiment, the swelling or thickening agent which can be contained in the composition is selected, for example and not restricted to, from the group formed by montmorillonites, chalk, zeolites, silicic acids, bentonites, polycarboxylates and its acids, polyacrylates, polyacetals, dextrins, phosphonates, agar, carraghenates, gum tragacanth, xanthan gum, gum arabic, alginates, pectins, polyoses, guar flour, carob seed flour, starch, gelatin, casein, vinyl polymers, polyethers, polyimines, polyamides, polyurethanes, vinyl acetate/crotonic acid copolymers, vinylpyrrolidone/vinyl acrylate copolymers, vinyl acetate/butyl maleate/isobornyl acrilate copolymers, methylvinylether/maleic anhydride acid copolymers and their esters, polyvinylpyrrolidone, vinylpyrrolidone/vinyl acetate copolymers, cellulose ethers such as tyloses, carboxymethylcellulose and hydroxyethylcellulose, silicone, polyethylene glycol monoesters and diesters with a high molecular weight and fatty acids, polyacrylamides, polyvinylic alcohol and mixtures thereof. Preferably the composition is a washing agent or a spray.

In another particular embodiment, the consistency-generating agent which can be contained in the composition is selected, for example and not restricted to, from the group formed by fatty alcohols or hydroxy fatty alcohols with from 12 to 22 carbon atoms, partial glycerides, fatty acids or hydroxy fatty acids, alkyl oligo glucosides and/or fatty acid N-methyl glucamides, polyglycerin poly-12-hydroxy stearates or mixtures thereof. The composition is preferably a washing agent or a spray.

In another particular embodiment, the whitening or textile material bleaching activator which can be contained in the composition is selected, for example and not restricted to, from the group formed by transition metal salts, or transition metal complexes which intensify the bleaching, such as manganese carbonyl complexes, iron, cobalt, ruthenium or molybdenum, bleach catalysts of manganese complexes, iron, cobalt, ruthenium, molybdenum, titanium, vanadium or copper with amine ligands, peroxo carboxyl aliphatic acids preferably with from 1 to 10 carbon atoms, perbenzoic acid, polyacylated alkylene diamines, such as tetraacetylethylenediamine (TAED), acylated triazine derivatives, such as 1,5-diacetyl-2,4-dioxohexahydro-1,3,5-triazine (DADHT), acylated glycoluril, such as tetraacetylglycoluril (TAGU), N-acylimides such as N-nonanoyl succinimide (NOSI), acylated phenol sulfonates, such as n-nonanoyl sulfonate- or iso-nonanoyloxy benzene (n-, or iso-NOBS), acylated carboxylic acid anhydrides, such as triethyl o-acetyl citrate (TEOC), carboxylic acid anhydrides, such as phthalic acid anhydride, isatoic acid anhydride and/or succinic acid anhydride; carboxylic acid amides, such as N-methyldiacetamide, glycolide, acylated polyvalent alcohols, such as triacetin, ethylene glycol diacetate, isopropenyl acetate, 2,5-diacethoxy-2,5-dihydrofuran and enol esters, as well as acetylated sorbitol and mannitol, acetylated sugar derivatives, in particular pentaacetyl glucose (PAG), pentaacetyl fructose, tetraacetyl xylose, and octaacetyl lactose, as well as glucamine, or gluconolactone or derivatives thereof, caprolactams or derivatives thereof such as N-benzoyl caprolactam and N-acetyl caprolactam, acyl acetates with substitute hydrophilic acyl lactam, nitryl derivatives, such as cyanopyridines, Nitrilquats, for example N-alkylammonium acetonitrile and/or cyanamide derivatives and/or combinations of conventional bleaching activators, sodium percarbonate, sodium perborate tetrahydrate and sodium perborate monohydrate, peroxypyrophosphates, citrate perhydrates, peracid salts or peroxy acids which provide H2O2, such as persulfates, salts sold under the trade name CAROAT®, or persulfuric acid; urea peroxyhydrate percarbamide, typical organic bleaching agents such as diacyl peroxides, for example dibenzoyl peroxide; peroxy acids, for example alkyl peroxy acids and aryl peroxy acids. Preferably peroxybenzoic acid and derivatives thereof substituted in the ring can be used, such as alkyl peroxybenzoic acids; peroxy-α-naphthoic acid and magnesium monoperphthalate, aliphatic peroxy acids or substituted aliphatic acids such as peroxylauric acid, peroxystearic acid, γ-phthalimido peroxycapronic acid (phthalimido peroxy hexanoic acid PAP), o-carboxy benzamido peroxycapronic acid, N-nonenylamidoperadipic acid and N-nonenylamidopersuccinates, and aliphatic peroxy dicarboxylic acids (preferably with 1 to 10 carbon atoms, in particular 2 to 4 carbon atoms) and araliphatic peroxy dicarboxylic acids, such as 1,12-diperoxycarboxylic acid, 1,9-diperoxyazelaic acid, diperoxysebacic acid, diperoxy brassylic acid, diperoxyphtalic acids, 1,4-diacid-2-decyl diperoxy butanoic and N,N-terephthaloyl-di(6-aminopercaproic acid). In principle, substances which release chlorine or bromine can also be used as bleaching agents. Among the suitable materials which release chlorine or bromine the following are considered, for example: heterocyclic N-bromo- and N-chloro amides, for example, trichloroisocyanuric acid, tribromoisocyanuric acid, dibromoisocyanuric acid and/or dichloroisocyanuric acid (DICA) and/or their salts with cations, such as potassium and sodium. Compounds of hydantoin, such as 1,3-dichloro-5,5-dimethylhydantoin are equally suitable. More preferable are sodium 4-(octanoyloxy)-benzenesulfonate, n-nonanoyl- or iso-nonanoyloxybenzenesulfonate (n- or iso-NOBS), undecenoyloxybenzenesulfonate (UDOBS), sodium dodecanoyloxybenzenesulfonate (DOBS), decanoyloxybenzoic acid (DOBA, OBC 10) and/or dodecanoyloxibenzenesulfonate (OBS 12), as well as N-methyl morpholinium acetonitrile (MMA). Preferably the composition is a washing agent or a spray.

Likewise, the hydrophilization agent which may be contained in the composition is selected, for example and not restricted to, from the group formed by alcohols, polyols, polyethylene glycols, alkanolamines, glycol mono- or polyvalent ether, carboxylates or copolymers in blocks of oxide of ethylene oxide-propylene, provided that they are miscible with water. The hydrophilized agents are preferably selected from ethanol, n- or iso-propanol, butanols, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl ethyl- or -propyl ether, dipropylene glycol monomethyl- or -ethyl ether, diisopropylene glycol monomethyl- or -ethyl ether, methoxy, ethoxy, or butoxytriglycol, 1-butoxyethoxy-2-propanol, 3-methyl-3-methoxybutanol, propylene-glycol-t-butyl-ether, sorbitol, mannitol, or mixtures thereof. Preferably the composition is a washing agent or a spray.

An additional aspect of this invention relates to the use of the previous compositions, preferably in the form of washing agents or for the treatment of textile materials. In this invention textile materials are understood to be fabrics, non-woven fabrics, garments and medical devices. Within textile materials the preferred fabrics, non-woven fabrics, garments and medical devices are bandages, gauzes, t-shirts, socks, tights, underwear, girdles, gloves, diapers, sanitary napkins, dressings, bedspreads, wipes, hydrogels, adhesive patches, non-adhesive patches, microelectric patches and/or face masks.

A last aspect of this invention relates to the use of textile materials treated with liposomes which contain active ingredients and/or cosmetic and/or dermopharmaceutical adjuvants, and which are bound to cationic polymers, wherein these polymers form a network on the surface of the textile material when they come into contact with a textile material, or compositions or washing agents or sprays which contain these liposomes, for the treatment and/or care of the skin, hair and/or scalp. Preferably the treatment and/or care of the skin, hair and/or scalp is selected from the group formed by treatment and/or prevention of skin aging, healing of the skin and/or scalp, dermatological treatment of skin diseases, treatment and/or prevention of cellulitis, tanning of the skin, lightening of the color or bleaching of the skin and treatment and/or prevention of hair loss.

In the context of this invention, the term "aging" relates to the changes experienced by the skin with age (chrono-aging) or due to exposure to the sun (photoaging) or to environmental agents such as tobacco smoke, extreme climatic conditions of cold and wind, chemical pollutants or pollution, and includes all the external visible changes as well as those noticeable by palpation, for example and not restricted to, the development of discontinuities on the skin such as wrinkles, fine lines, furrows, irregularities or roughness, increase in the size of pores, loss of elasticity, loss of firmness, loss of smoothness, loss of the capacity to recover from the deformation, sagging of the skin such as sagging cheeks, the appearance of bag under the eyes or the appearance of a double chin among others, changes to the color of the skin such as marks, reddening, bags under the eyes, appearance of hyperpigmented areas such as age spots or freckles among others, anomalous differentiation, hyperkeratinization, elastosis, keratosis, hair loss, orange-peel skin, loss of collagen structure and other histological changes of the stratum corneum, of the dermis, epidermis, vascular system (for example the appearance of spider veins or telangiectasias) or of those tissues close to the skin, among others.

The following specific examples provided herein serve to illustrate the nature of this invention. These examples are included solely for illustrative purposes and should not be construed as limitations on the invention claimed herein.

DESCRIPTION OF THE FIGURES

FIG. 1 shows 5 different textile materials (nonwoven viscose, polyamide, tights, cotton and polyester), the quantity of caffeine bound to the textile material as per quantity of caffeine in the bath where the textile material is submerged for 3 bathings wherein the textile material weight/bath ratios are 1/25 (top graph), 1/50 (middle graph) and 1/100 (bottom graph). Caffeine is one of the cosmetic and/or dermopharmaceutical active ingredients contained in the liposomes of example 3.

FIG. 2 shows the quantity of caffeine bound to the textile material as per quantity of caffeine in the bath where the textile material is submerged for 3 bathings wherein the textile material weight/bath ratios are 1/25 (top graph), 1/50 (middle graph) and 1/100 (bottom graph), for the same textile materials as FIG. 1, after 2 washes of the textile material.

FIG. 4 shows images of liposomes from example 2 through transmission electron microscopy (TEM).

FIG. 5a shows the image of the mica substrate used for atomic force microscopy. FIG. 5b shows the atomic force microscopy image of the liposomes bound to cationic polymers from example 2. The irregularities concern the cationic polymers which form the network and the clearer, flatter and higher zones concern the liposomes bound to these cationic polymers.

DETAILED DESCRIPTION

Figure 1:
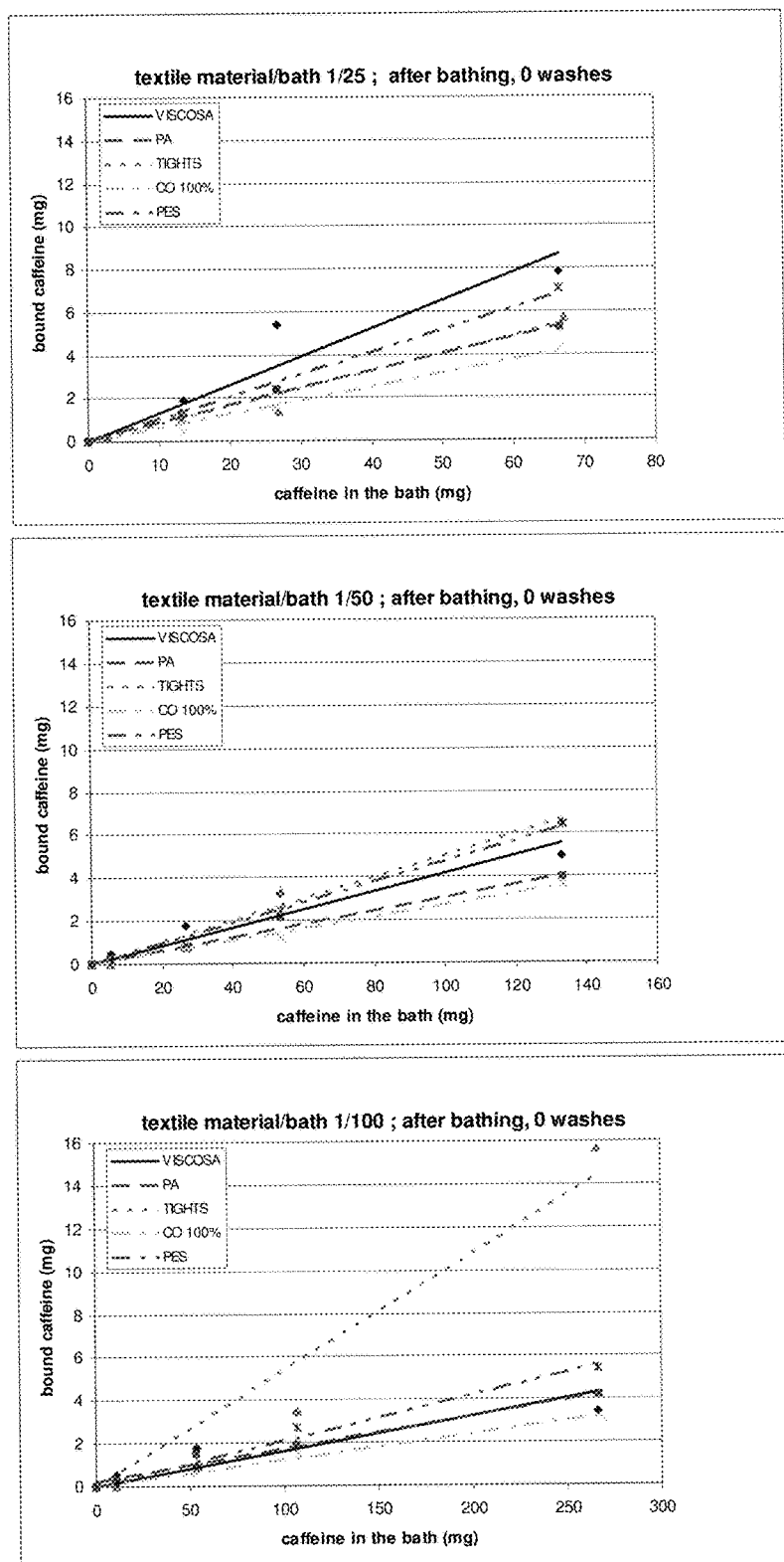
FIG. 1.
Figure 2:
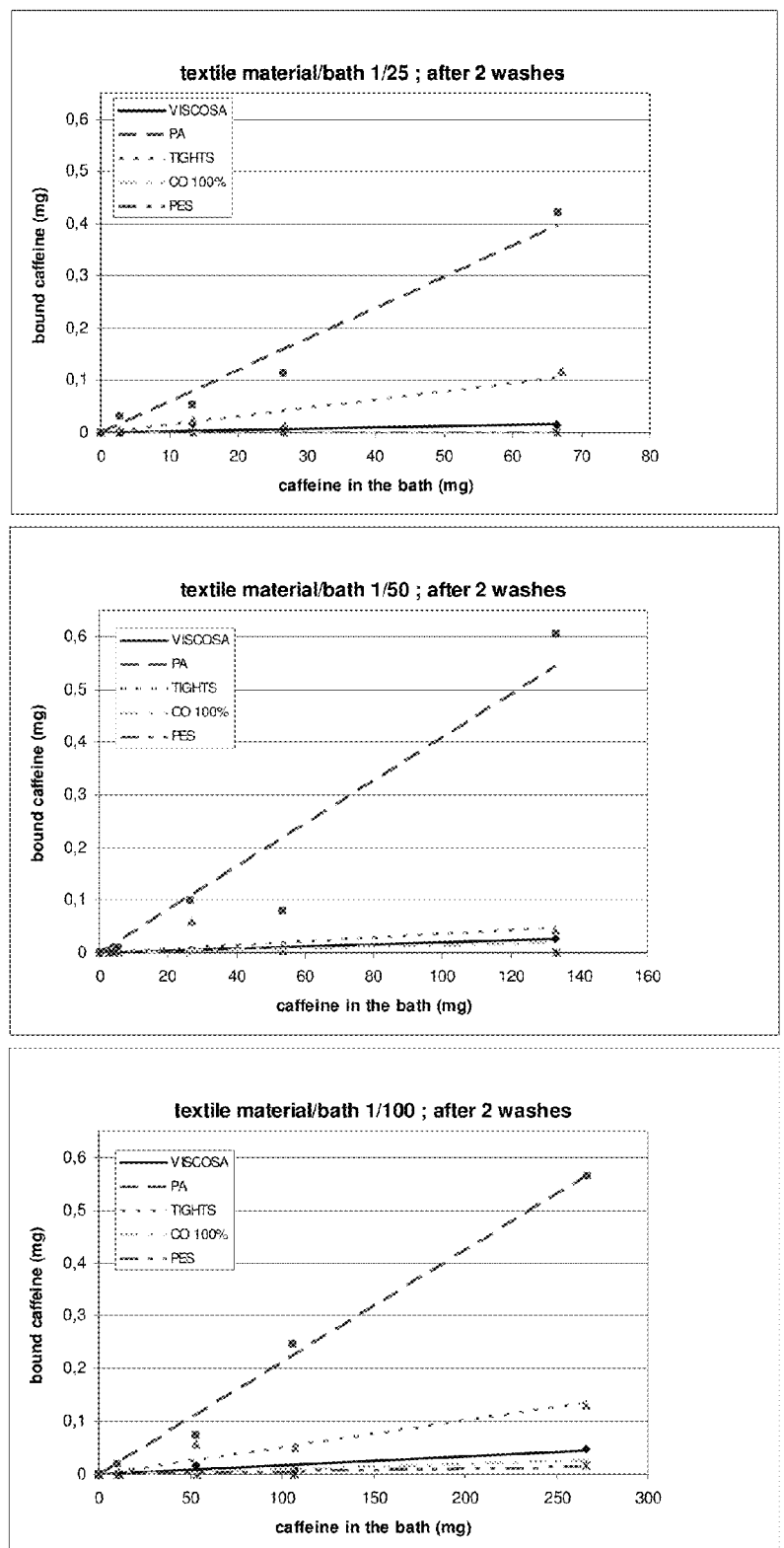
FIG. 2.
Figure 3:
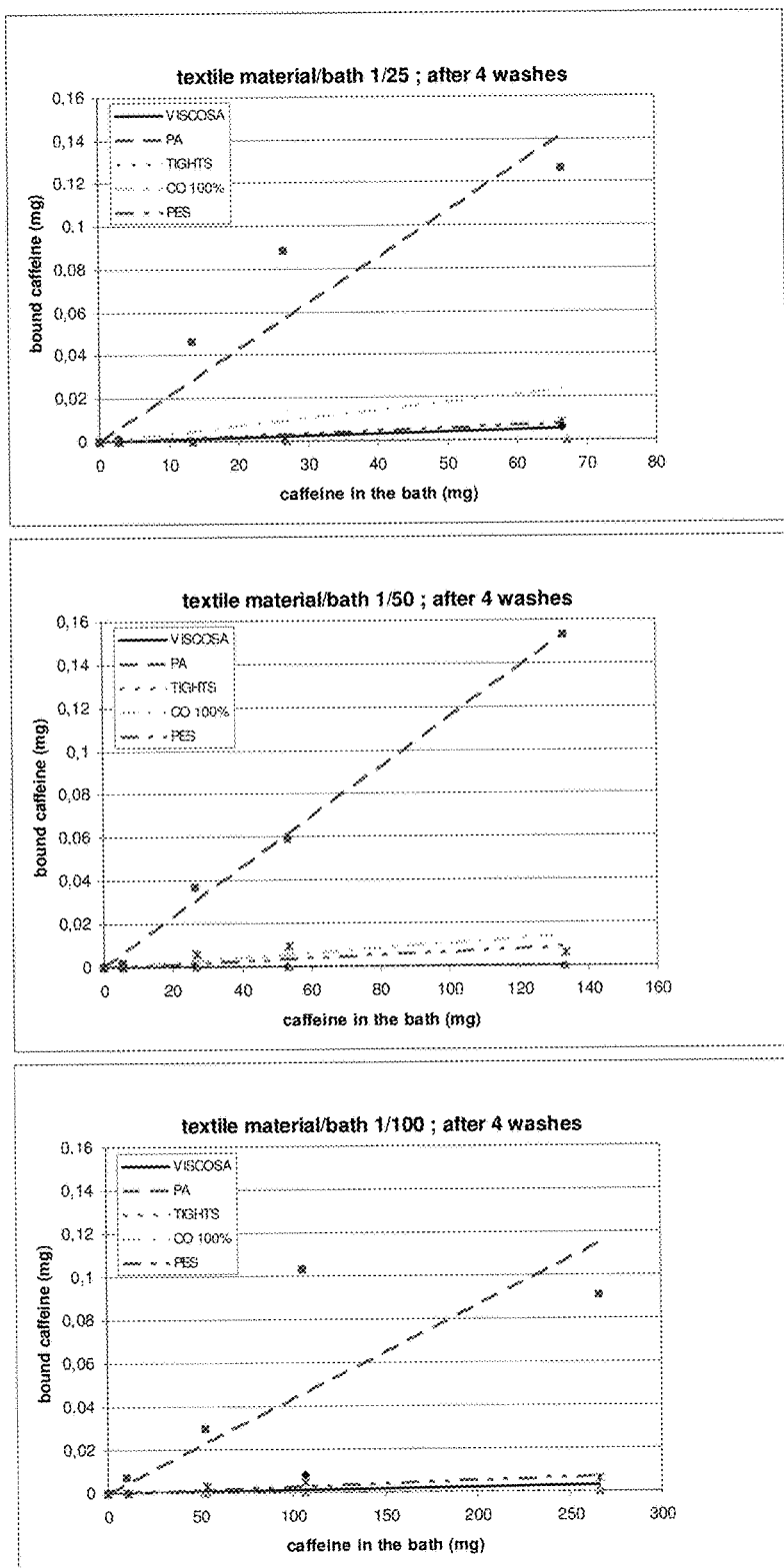
FIG. 3: shows the quantity of caffeine bound to the textile material as per quantity of caffeine in the bath where the textile material is submerged for 3 bathings wherein the textile material weight/bath ratios are 1/25 (top graph), 1/50 (middle graph) and 1/100 (bottom graph), for the same textile materials as FIG. 1, after 4 washes of the textile material.
Figure 4:
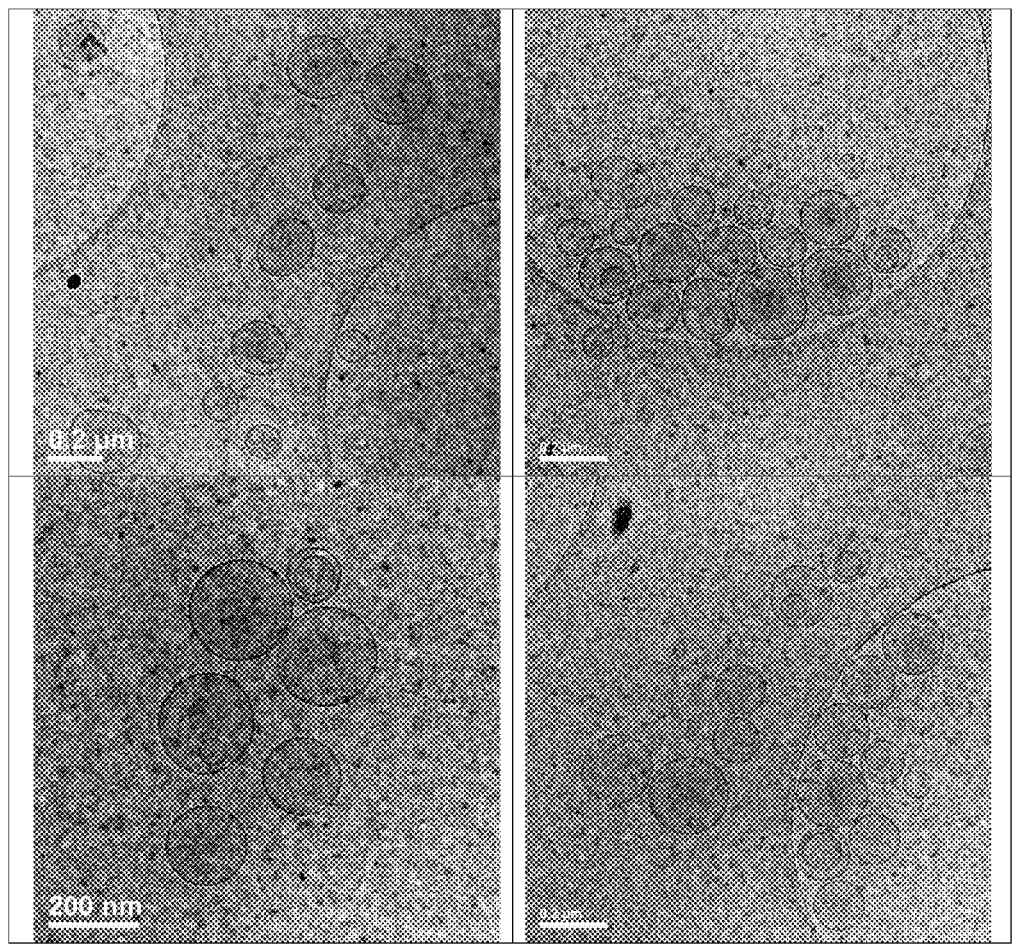
FIG. 4.
Figure 5:
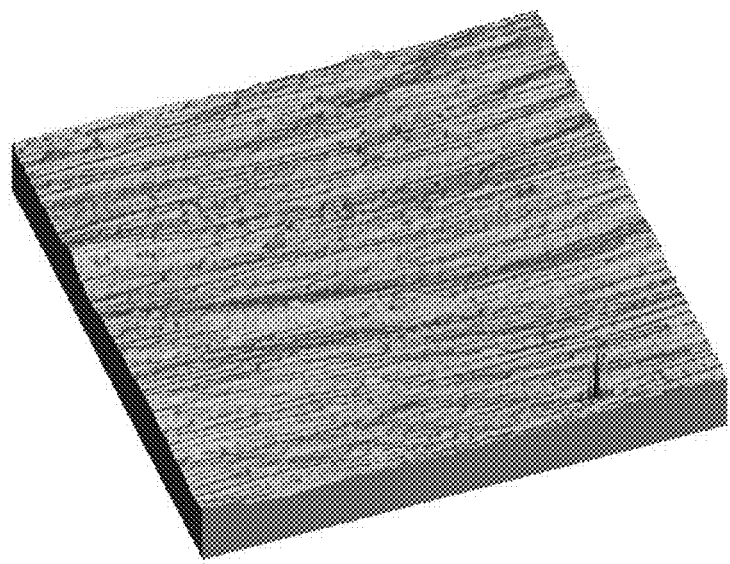
FIG. 5.
Figure 5:
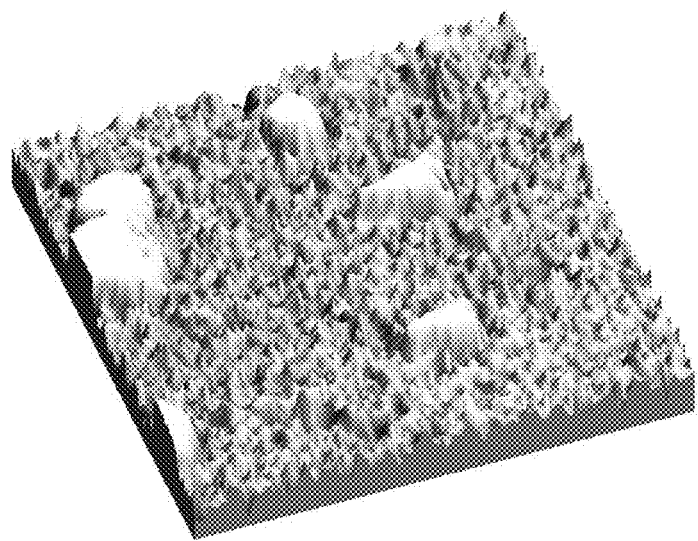

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

EXAMPLES

General Methodology

All the reagents and solvents are of synthesis quality and are used without any additional treatment.

Example 1

Obtaining liposomes containing Antarcticine bound to cationic polymers of polyquaternium-16

Antarcticine® (phase A), water, Zemea [INCI: 1,3-propanediol] and phenoxyethanol (ingredients B to D) were added to a suitable vessel. When all the previous components had dissolved Centrolex F [INCI: Lecithin] (ingredient E) was slowly added under intense stirring until it was completely dissolved. Afterwards Labrasol [INCI: PEG-8 Caprylic/Capric Glycerides] (ingredient F) was added and was left being stirred for 10-15 minutes to form an emulsion.

|   | INGREDIENT (INCI Nomenclature) | % IN WEIGHT |
|---|---|---|
| A | *PSEUDOALTEROMONAS* FERMENT EXTRACT | 2.5 |
| A | PHENOXYETHANOL, METHYLPARABEN, BUTYLPARABEN, ETHYLPARABEN, PROPYLPARABEN, ISOBUTYLPARABEN | 0.05 |
| B | 1,3-PROPANEDIOL | 8.50 |
| C | PHENOXYETHANOL | 1.70 |
| D | AQUA (WATER) | q.s.p. 100 |
| E | LECITHIN | 10.00 |
| F | PEG-8 CAPRYLIC/CAPRIC GLYCERIDES | 4.00 |

The sample was passed through a microfluidizer for a cycle at an entrance pressure of 80 bar and 12500 psi on exit. The liposomes obtained were added to Luviquat HMM552 [INCI: Polyquaternium-16] in a cationic liposome:polymer ratio of 1.5:1 under light stirring.

Example 2

Obtaining liposomes containing Decelerine™ bound to cationic polymers of polyquaternium-16

The liposomes were obtained in the same way as in example 1 but instead of Antarcticine®, Decelerine™ (ingredients from phase A) was used and the same ingredients and quantities as in the other phases.

|   | INGREDIENT (INCI Nomenclature) | % IN WEIGHT |
|---|---|---|
| A | GLYCERIN | 1.00 |
| A | BARBADOS ALOE (*ALOE BARBADENSIS*) LEAF EXTRACT, SODIUM SORBATE, SODIUM BENZOATE | 1.00 |
| A | LAURYL ISOQUINOLIUM BROMIDE, ISOPROPYL ALCOHOL | 0.50 |
| A | *PSEUDOALTEROMONAS* FERMENT EXTRACT | 0.25 |
| A | POLYQUATERNIUM-37 | 0.20 |

-continued

| | INGREDIENT (INCI Nomenclature) | % IN WEIGHT |
|---|---|---|
| A | DISODIUM EDTA | 0.18 |
| A | ALLANTOIN | 0.05 |
| A | GLUCOSE | 0.005 |
| A | CAPRYLYL GLYCOL | 0.005 |
| B | 1,3-PROPANEDIOL | 8.50 |
| C | PHENOXYETHANOL | 1.70 |
| D | AQUA (WATER) | q.s.p. 100 |
| E | LECITHIN | 10.00 |
| F | PEG-8 CAPRYLIC/CAPRIC GLYCERIDES | 4.00 |

The liposomes obtained were added to Luviquat HMM552 [INCI: Polyquaternium-16] in a cationic liposome:polymer ratio of 1.5:1 under light stirring.

Example 3

Obtaining liposomes containing Liporeductyl bound to cationic polymers of polyquaternium-16

The liposomes were obtained in the same way as in example 1 but instead of Antarcticine®, Liporeductyl® (ingredients from phase A) was used and the same ingredients and quantities as in the other phases.

| | INGREDIENT (INCI Nomenclature) | % IN WEIGHT |
|---|---|---|
| A | GLYCERIN | 1.00 |
| A | BUTCHERBROOM (RUSCUS ACULEATUS) ROOT EXTRACT, MALTODEXTRIN, SILICA | 0.57 |
| A | LECITHIN | 0.83 |
| A | CAFFEINE | 0.59 |
| A | TEA-HYDROIODIDE | 0.44 |
| A | CARNITINE | 0.30 |
| A | BUTYLENE GLYCOL, WATER (AQUA), IVY (HEDERA HELIX) | 0.38 |
| A | ESCIN | 0.74 |
| A | TRIPEPTIDE-1 | 0.001 |
| A | XANTHAN GUM | 0.04 |
| A | CARRAGEENAN (CHONDRUS CRISPUS) | 0.005 |
| A | CAPRYLYL GLYCOL | 0.09 |
| A | PHENOXYETHANOL | 0.09 |
| A | POTASSIUM SORBATE | 0.03 |
| B | 1,3-PROPANEDIOL | 8.50 |
| C | PHENOXYETHANOL | 1.70 |
| D | AQUA (WATER) | q.s.p. 100 |
| E | LECITHIN | 10.00 |
| F | PEG-8 CAPRYLIC/CAPRIC GLYCERIDES | 4.00 |

The liposomes obtained were added to Luviquat HMM552 [INCI: Polyquaternium-16] in a cationic liposome:polymer ratio of 1.5:1 under light stirring.

Example 4

Obtaining liposomes containing Serilesine® bound to cationic polymers of polyquaternium-16

The liposomes were obtained in the same way as in example 1 but instead of Antarcticine®, Serilesine® (ingredients from phase A) was used and the same ingredients and quantities as in the other phases.

| | INGREDIENT (INCI Nomenclature) | % IN WEIGHT |
|---|---|---|
| A | GLYCERIN | 1.00 |
| A | HEXAPEPTIDE-10 | 0.005 |

-continued

| | INGREDIENT (INCI Nomenclature) | % IN WEIGHT |
|---|---|---|
| A | CAPRYLYL GLYCOL | 0.05 |
| B | 1,3-PROPANEDIOL | 8.50 |
| C | PHENOXYETHANOL | 1.70 |
| D | AQUA (WATER) | q.s.p. 100 |
| E | LECITHIN | 10.00 |
| F | PEG-8 CAPRYLIC/CAPRIC GLYCERIDES | 4.00 |

The liposomes obtained were added to Luviquat HMM552 [INCI: Polyquaternium-16] in a cationic liposome:polymer ratio of 1.5:1 under light stirring.

Example 5

Obtaining liposomes containing hyaluronic acid and D-panthenol bound to cationic polymers of polyquaternium-16

Water, Zemea [INCI: 1,3-propanediol] and phenoxyethanol (ingredients C to E) were added to a suitable vessel. When all the previous components had dissolved hyaluronic acid was added (ingredient A) slowly under light stirring. When it had dissolved, the D-panthenol (ingredient B) was added. Afterwards Leciflor 100IP [INCI: Lecithin] (ingredient F) was added slowly under intense stirring until fully dissolved. Next Labrasol [INCI: PEG-8 Caprylic/Capric Glycerides] (ingredient G) was added and was left stirring for 10-15 minutes so an emulsion was formed.

| | INGREDIENT (INCI Nomenclature) | % IN WEIGHT |
|---|---|---|
| A | HYALURONIC ACID | 0.05 |
| B | DIETHYLAMINOHYDROXYBENZOYL HEXYL BENZOATE | 8.50 |
| C | 1,3-PROPANEDIOL | 8.50 |
| D | PHENOXYETHANOL | 1.70 |
| E | AQUA (WATER) | q.s.p. 100 |
| F | LECITHIN | 10.00 |
| G | PEG-8 CAPRYLIC/CAPRIC GLYCERIDES | 4.00 |

The liposomes obtained were added to Luviquat HMM552 [INCI: Polyquaternium-16] in a cationic liposome: polymer ratio of 1.5:1 under light stirring.

Example 6

Obtaining liposomes containing Lipochroman-6, Preventhelia™, Parsol MCX and Uvinul® A Plus bound to cationic polymers of polyquaternium-16

Preventhelia™ (ingredients from phase A), part of the water, Zemea [INCI: 1,3-propanediol], Labrasol [INCI: PEG-8 Caprylic/Capric Glycerides] and phenoxyethanol (ingredients B to E) were added to a suitable vessel. When all the previous components had dissolved Leciflor 100IP [INCI: Lecithin] (ingredient F) was added slowly under intense stirring until fully dissolved. In another vessel Uvinul® A Plus [INCI: Diethylamino Hydroxybenzoyl Hexyl Benzoate], Parsol MCX [INCI: Ethylhexyl methoxycinnamate], Lipochroman-6 [INCI: Dimethylmethoxy Chromanol] (ingredients G to I) and the rest of the water were mixed together, heated to 60° C. to dissolve them. The second mixture was added to the first slowly under intense stirring.

| | INGREDIENT (INCI Nomenclature) | % IN WEIGHT |
|---|---|---|
| A | DIAMINOPROPIONOYL TRIPEPTIDE-33 | 0.0043 |
| A | CAPRYLYL GLYCOL | 0.043 |
| B | 1,3-PROPANEDIOL | 8.50 |
| C | PEG-8 CAPRYLIC/CAPRIC GLYCERIDES | 4.00 |
| D | PHENOXYETHANOL | 1.70 |
| E | AQUA (WATER) | q.s.p. 100 |
| F | LECITHIN | 10.00 |
| G | DIETHYLAMINO HYDROXYBENZOYL HEXYL BENZOATE | 5.00 |
| H | ETHYLHEXYL METHOXYCINNAMATE | 5.00 |
| I | DIMETHYLMETHOXY CHROMANOL | 0.085 |

The sample was passed through a microfluidizer for 3 cycles at an entrance pressure of 80 bar and 12500 psi on exit. The liposomes obtained were added to Luviquat HMM552 [INCI: Polyquaternium-16] in a cationic liposome: polymer ratio of 1.5:1 under light stirring.

Example 7

Composition of a spray containing liposomes which contain Antarcticine bound to cationic polymers Antarcticine® (phase A), water, Zemea [INCI: 1,3-propanediol] and phenoxyethanol (ingredients B to D) were added to a suitable vessel. When all the previous components had dissolved it was heated to 40° C. and Emulmetik 320 [INCI: Hydrogenated Lecithin] (ingredient E) was added slowly under intense stirring until fully dissolved.

| | INGREDIENT (INCI Nomenclature) | % IN WEIGHT |
|---|---|---|
| A | *PSEUDOALTEROMONAS* FERMENT EXTRACT | 0.78 |
| A | PHENOXYETHANOL, METHYLPARABEN, BUTYLPARABEN, ETHYLPARABEN, PROPYLPARABEN, ISOBUTYLPARABEN | 0.01 |
| B | 1,3-PROPANEDIOL | 8.50 |
| C | PHENOXYETHANOL | 1.125 |
| D | AQUA (WATER) | q.s.p. 100 |
| E | HYDROGENATED LECITHIN | 0.85 |

The sample was passed through a microfluidizer for 3 cycles at an entrance pressure of 80 bar and 12500 psi on exit. The liposomes obtained were added to Luviquat HMM552 [INCI: Polyquaternium-16] in a cationic liposome:polymer:water ratio of 8:1:1 under light stirring.

Example 8

Composition of a spray containing liposomes which contain Antarcticine bound to cationic polymers Antarcticine® (phase A), water, Zemea [INCI: 1,3-propanediol] and phenoxyethanol (ingredients B to D) were added to a suitable vessel. When all the previous components had dissolved it was heated to 40° C. and Emulmetik 320 [INCI: Hydrogenated Lecithin] (ingredient E) was added slowly under intense stirring until fully dissolved.

| | INGREDIENT (INCI Nomenclature) | % IN WEIGHT |
|---|---|---|
| A | *PSEUDOALTEROMONAS* FERMENT EXTRACT | 1.56 |
| A | PHENOXYETHANOL, METHYLPARABEN, BUTYLPARABEN, ETHYLPARABEN, PROPYLPARABEN, ISOBUTYLPARABEN | 0.03 |
| B | 1,3-PROPANEDIOL | 8.50 |
| C | PHENOXYETHANOL | 1.125 |
| D | AQUA (WATER) | q.s.p. 100 |
| E | HYDROGENATED LECITHIN | 0.85 |

The sample was passed through a microfluidizer for 3 cycles at an entrance pressure of 80 bar and 12500 psi on exit. The liposomes obtained were added to Luviquat HMM552 [INCI: Polyquaternium-16] in a cationic liposome: polymer ratio of 4:1 under light stirring.

Example 9

Liposomes bound to cationic polymers containing Lipore-ductyl in textile materials, their washing and resistance to washing.

The liposomes from example 3 were diluted in 50 mL water baths at 1%, 5%, 10% and 25% in weight. Different textile materials, such as polyamide (PA), cotton (CO 100%), polyester (PES), non-woven viscose (VISCOSA) and tights (TIGHTS), were submerged in each of the previous baths with ratios of textile material weight/bath of 1/25, 1/50 and 1/100 and they were kept submerged for 10 minutes at room temperature without stirring.

To test the resistance of the washing of the liposomes adhered to the previous textile materials they were treated with detergent solutions under stirring according to standard ISO 105 CO6. The quantities of active ingredient bound to the textile material after the bath and after a number of washes were determined after the extraction of caffeine from the textile material through sonication for 10 minutes in a solution of pH 3.0. Afterwards it was heated and maintained at 60° C. for 30 minutes. The external phase was filtered (0.45 μm) and was analyzed by the HPLC-UV/VIS detector. The quantities of caffeine are shown in FIGS. 1 to 3.

The textile materials were dried by being hung out according to standard UNE-EN ISO 6330 after the bath and after each wash. Typical drying times were 24 hours at room temperature.

Example 10

Transmission electron microscopy of liposomes which contain Decelerine™ bound to cationic polymers.

Images of liposomes from example 2 were taken using transmission electron microscopy (TEM) (FIG. 4). The presence of mono- and bilaminar spherical vesicles of 100 to 300 nm in diameter was observed. The cationic polymer chains of polyquaternium-16 could not be observed by this microscopy technique. The difference in the measurements according to this technique and dynamic light scattering is consistent with a structure wherein the liposome is embedded in a cationic network of cationic polymers.

Example 11

Atomic Force Microscopy of liposomes which contain Decelerine™ bound to cationic polymers.

Images of liposomes from example 2 were taken by atomic force microscopy. FIG. 5*a* shows an image of the mica substrate on its own. As the mica does not present any distortion on its structure, the color pattern is homogeneous. However, for the liposomes in example 2, FIG. 5*b* shows a layer with series of irregularities or small peaks which are the polyquaternium-16 layer or film on the mica substrate. Furthermore, vesicular structures in a clearer color than the liposomes to which the polyquaternium-16 polymeric chains are bound were observed.

Example 12

Test of transfer to skin of the active ingredients contained in liposomes of Liporeductyl® in textile materials.

The liposomes obtained in example 3 were taken and 100 µL of 2% weight aqueous solution of these liposomes was applied directly with a micropipette to a piece of cotton fabric with a surface area of 1,77 cm2.

Next the transfer test was carried out with pig skin, in accordance with a modification of the OCDE standard 428 (Skin absorption: in vitro method). The modification consisted of applying a weight to the fabric sample placed on the pig skin to simulate the pressure that the skin would exert on the fabric. The weight applied was 1 g. After 24 hours of exposure of the cotton fabric to the skin the quantity of caffeine to have reached the surface of the skin as well as the different layers of skin was determined by HPLC. It was obtained that with a pressure even as small as 0.56 g/cm2, the percentage of caffeine which passed through the surface and layer of skin was 0.40%.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A textile material with adsorbed liposomes of a size smaller than or equal to 200 nm, which contain at least one phospholipid and cosmetic and/or dermopharmaceutical active ingredients and/or adjuvants, the liposomes being bound to cationic copolymers of acrylic acid with dimethyldiallylammonium chloride, each of the cationic copolymers having positive charges which each electrostatically interact with a phosphate group of the phospholipids which form lipid membranes of the liposomes, each of the cationic copolymers being of a particle size of between 600 and 1700 nm, such that the same cationic copolymer interacts with several of the liposomes bound thereto at once and is bound to a surface of the textile material at several points, and wherein the cationic copolymers form a network of polymer chains over a surface of the textile material, in which the liposomes are embedded.

2. The textile material according to claim 1, wherein the phospholipid of the liposomes is a phosphoglyceride.

3. The textile material according to claim 2, wherein the phosphoglyceride is selected from the group consisting of phosphatidylserine, phosphatidylinositol, phosphatidylethanolamine, phosphatidylcholine, phosphatidic acid, phosphatidylglycerol, diphosphatidylglycerol, phosphorylcholine, their fatty acid esters, hydrogenation products and mixtures thereof.

4. The textile material according to claim 1, wherein the liposomes are formed by one or more phospholipids and one or more surfactants.

5. The textile material according to claim 4, wherein the surfactant is selected from the group consisting of nonionic surfactants, amphoteric surfactants, anionic surfactants, cationic surfactants and mixtures thereof.

6. The textile material according to claim 5, wherein the surfactant is an anionic surfactant.

7. The textile material according to claim 1 wherein the cationic copolymer includes polyquaternium-16.

8. The textile material according to claim 1, wherein the liposomes are microfluidized liposomes.

* * * * *